Figure 1:
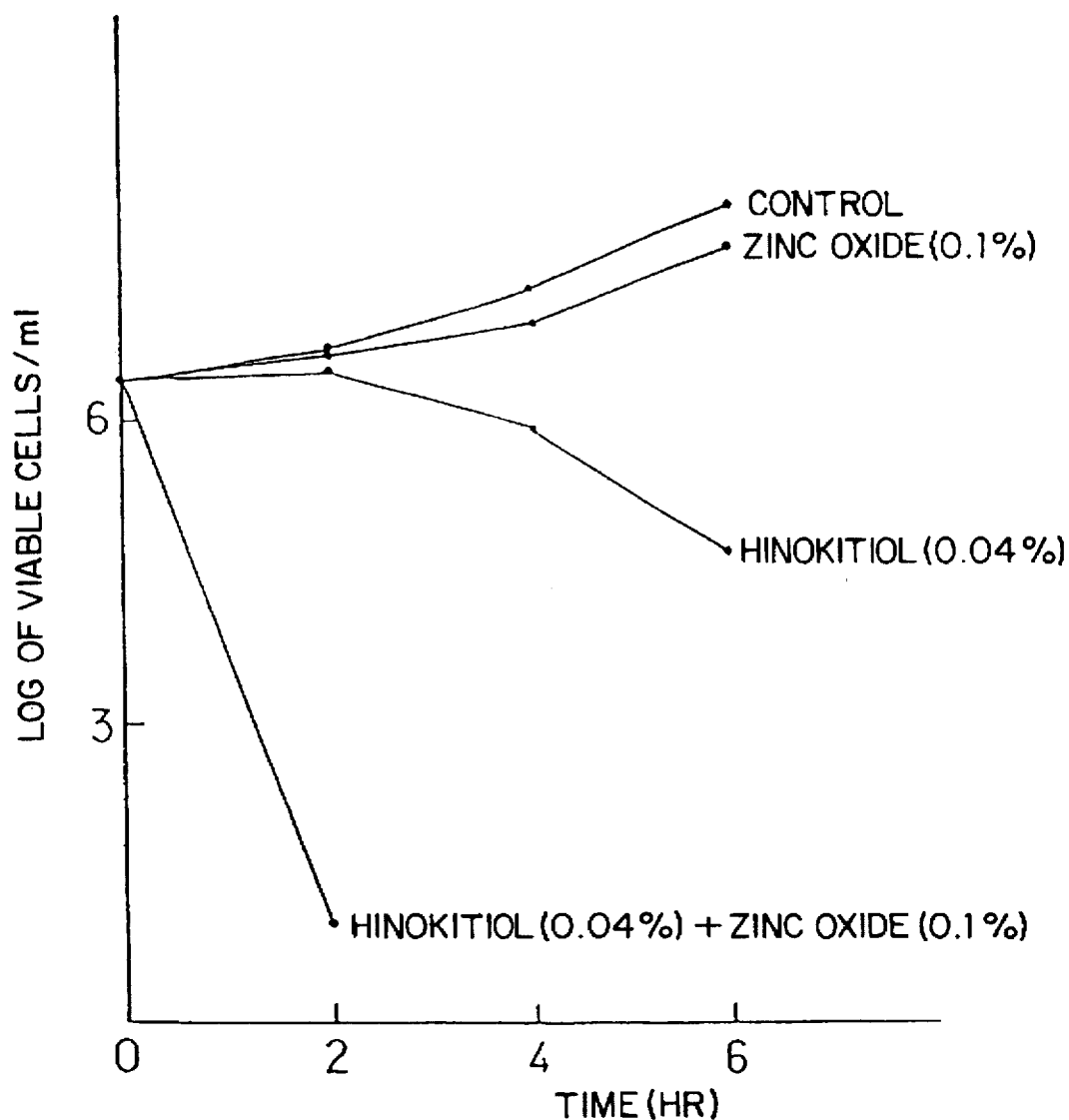

United States Patent [19]

Otsu et al.

[11] Patent Number: 5,696,169
[45] Date of Patent: Dec. 9, 1997

[54] ANTIBACTERIAL AND ANTIFUNGAL ACTIVITY METHOD, THERAPEUTIC METHOD OF INFECTIOUS DISEASES AND PRESERVING METHOD OF COSMETICS

[75] Inventors: Yoshiro Otsu, Minoo; Yaeno Arima, Kobe; Yoriko Nakai, Hyogo-ken, all of Japan

[73] Assignee: Otsuka Pharmaceutical Co., Ltd., Tokyo, Japan

[21] Appl. No.: 206,151

[22] Filed: Mar. 7, 1994

Related U.S. Application Data

[63] Continuation-in-part of Ser. No. 146,127, Nov. 12, 1993, abandoned.

[30] Foreign Application Priority Data

Aug. 23, 1993 [JP] Japan .................. 5-207548

[51] Int. Cl.$^6$ .......................... A61K 31/12; A61K 33/30
[52] U.S. Cl. .................. 514/675; 424/641; 424/642; 424/643; 514/844; 514/846
[58] Field of Search ................ 424/195.1, 641, 424/642, 643; 514/844, 852, 858, 859, 675

[56] References Cited

U.S. PATENT DOCUMENTS

| | | | |
|---|---|---|---|
| 4,361,581 | 11/1982 | Fukuda | 424/312 |
| 5,009,898 | 4/1991 | Sakuma et al. | 424/618 |
| 5,096,697 | 3/1992 | Adachi et al. | 424/47 |
| 5,215,995 | 6/1993 | Honbo et al. | 514/291 |
| 5,219,847 | 6/1993 | Taguchi et al. | 514/188 |
| 5,268,174 | 12/1993 | Sakuma et al. | 424/195.1 |

FOREIGN PATENT DOCUMENTS

| | | |
|---|---|---|
| 3443985 | 6/1986 | Germany . |
| 3932469 | 4/1990 | Germany . |
| 49-1718 | 1/1974 | Japan . |
| 56-8309 | 1/1981 | Japan . |
| 61-238716 | 10/1986 | Japan . |
| 61-238718 | 10/1986 | Japan . |
| 61-263910 | 11/1986 | Japan . |
| 62-053917 | 3/1987 | Japan . |
| 62-93215 | 4/1987 | Japan . |
| 2157201 | 6/1990 | Japan . |
| 2243607 | 9/1990 | Japan . |
| 5271064 | 10/1993 | Japan . |
| 8701281 | 3/1987 | WIPO . |

OTHER PUBLICATIONS

Okabe et al. *Fragrance J.*, vol. 17(2): 74–79, (1989) Abstract Only.
Domsch et al. *Parfuem. Kosmet.*, vol. 69(5): 272–4 & 276–8, (1988) Abstract Only.
Yakuji Nippou-sha, New Medicines of Today, vol. 17, p. 239, 1966.
European Search Report (EP 93 90 5631) dated Nov. 23, 1994–(JP–A–63 211 218 (Nippon Zeora K.K.) 2 Sep. 1988).
*Patent Abstracts of Japan*, vol. 12, No. 501(C–556) (3348), 27 Dec., 1988.
Tetsumoto, Sogo *Tokai Reg. Fish. Res. Lab.*, Tokyo, Japan, vol. 56, pp. 95–107, (1968).
"Cosmetics" edited by Masato Suzuki and Yoshiko Kurata, vol. 3, published by Jan. 25, 1989 by Kabushiki Kaisha CMC, pp. 116(520)–118(522).
Sankei Shinbun article published in Japan on Jun. 13, 1993.

*Primary Examiner*—John Kight
*Assistant Examiner*—Howard C. Lee
*Attorney, Agent, or Firm*—Sughrue, Mion, Zinn, Macpeak & Seas, PLLC

[57] ABSTRACT

The present invention provides a method of controlling bacteria or fungi which comprises contacting therewith a zinc compound and at least one member selected from among hinokitiol and salts thereof; a method of treating infectious diseases caused by bacteria or fungi which comprises administering a zinc compound and at least one member selected from among hinokitiol and salts thereof; and a method of preserving cosmetics which comprises adding thereto a zinc compound and at least one member selected from among hinokitiol and salts thereof.

20 Claims, 2 Drawing Sheets

ANTIBACTERIAL AND ANTIFUNGAL ACTIVITY METHOD, THERAPEUTIC METHOD OF INFECTIOUS DISEASES AND PRESERVING METHOD OF COSMETICS

CROSS-REFERENCE TO RELATED APPLICATIONS

This application is a continuation-in-part of our patent application Ser. No. 08/146,127 filed Nov. 12, 1993 (PCT/JP93/00297), now abandoned.

TECHNICAL FIELD

This invention relates to a method of controlling bacteria or fungi, to a method of treating infectious diseases caused by bacteria or fungi, and to a method of preserving cosmetics.

BACKGROUND ART

Zinc oxide is generally applied to affected sites of the skin in eczema, dermatitis, abrasion, burn or the like as a local astringent, desiccant and protectant and for relief of stimulations and absorption of secretion. This substance is used in various dosage forms, such as powder, solution, oil, lotion, liniment, ointment, paste, plaster and so on. Particularly, the ointment is used most generally.

Referring to the ointment, the Japanese Pharmacopoeia lists Zinc Oxide Ointment. However, this ointment has the drawback that because it does not contain any bactericide or preservative, the skin lesions become more susceptible to the infection of bacteria and fungi when it is repeatedly used over a long time.

Zinc oxide ointments supplemented with ichthammol, acrinol, boric acid or the like are also known. However, these ointments also have various drawbacks. Ichthammol, which is incorporated for reducing inflammation or relieving itching, has a peculiar odor and a brownish black color, so that zinc oxide ointments containing ichthammol have been delisted from the new Japanese Pharmacopeia (12th edition). Acrinol, which is incorporated for purposes of local sterilization or disinfection, may sometimes induce symptoms of irritation and has the drawback that it readily undergoes discoloration upon exposure to light and stains clothes yellow. Boric acid, which is incorporated for the purpose of sterilization, has only a weak inhibitory effect on bacterial growth and, when continuously used over a long period of time, it is absorbed through the skin and may cause poisoning, such as nausea and vomiting or diarrhea. Therefore, the use of this substance is rigorously controlled.

Furthermore, the above-mentioned various zinc oxide ointments containing antimicrobial agents are not sufficiently safe or low in irritation. Thus, they can hardly be applied to patients sensitive to irritation.

DISCLOSURE OF INVENTION

In view of the above state of the art, we made intensive investigations in an attempt to develop an antibacterial and antifungal agent having excellent antibacterial and antifungal activities. As a result, we found that when a zinc compound, inclusive of zinc oxide and the like, is used in combination with hinokitiol or a salt thereof, markedly improved antibacterial and antifungal activities are obtained. We also found that, due to these excellent antibacterial and antifungal activities, the combination of a zinc compound and hinokitiol or a salt thereof is very useful particularly for controlling bacteria or fungi, and therefore useful for treating infectious diseases caused by bacteria or fungi, for preserving cosmetics, and for other purposes. The present invention has been completed based on the above findings.

Thus, the invention is concerned with a method of controlling bacteria or fungi which comprises using or applying thereto or contacting therewith an effective amount of a zinc compound and an effective amount of hinokitiol or a salt thereof.

Particularly, the present invention provides a method of controlling bacteria comprising using or contacting therewith or applying thereto a bactericidally or bacteriostatically effective amount of a combination of a zinc compound and hinokitiol or a salt thereof. The present invention also provides a method of controlling fungi comprising using or contacting therewith or applying thereto a fungicidally or fungistatically effective amount of a combination of a zinc compound and hinokitiol or a salt thereof.

In the specification and claims, the expression "to control bacteria or fungi" is used to mean to produce antibacterial or antifungal effect, and thus means not only to kill or destroy bacteria or fungi (i.e., being bactericidal or fungicidal) but also to prevent or retard the growth of bacteria or fungi (i.e., being bacteriostatic or fungistatic).

Thus, the method of controlling bacteria or fungi includes, for example, external sterilization methods wherein a part or whole of human or animal bodies, general or medical articles or the like are sterilized by contacting them with the composition of the invention comprising a combination of a zinc compound and hinokitiol or a salt thereof, as well as bacteriostatic or fungistatic method wherein the growth of bacteria or fungi is prevented or retarded by said composition.

As a result of this effect of controlling bacteria or fungi, i.e., antibacterial or antifungal effect, the composition of the invention comprising a combination of a zinc compound and hinokitiol or a salt thereof is useful for treating infectious diseases caused by bacteria or fungi, for preserving cosmetics, and for other purposes.

Thus, the present invention provides a method of treating a patient with an infectious disease caused by bacteria or fungi which comprises administering to said patient an effective amount of a zinc compound and an effective amount of hinokitiol or a salt thereof.

The invention also provides the use of a combination of a zinc compound and hinokitiol or a salt thereof for producing an agent for treating infectious diseases caused by bacteria or fungi.

The invention further provides a method of preserving cosmetics which is characterized in that said cosmetics contain an effective amount of a zinc compound and an effective amount of hinokitiol or a salt thereof.

The invention is also concerned with antibacterial and antifungal compositions which comprise an effective amount of a zinc compound and an effective amount of hinokitiol or a salt thereof, and with cosmetics which contain an effective amount of a zinc compound and an effective amount of hinokitiol or a salt thereof.

In the practice of the invention, the zinc compound to be used is not limited to any particular species but includes a wide variety of per se known zinc compounds, such as, for example, zinc oxide, zinc chloride, zinc nitrate, zinc sulfate, zinc phosphate, zinc aluminate, zinc fluoride, zinc iodide, zinc hydroxide, zinc carbonate, zinc chromate, zinc benzoate, zinc acetate, zinc paraaminobenzoate, zinc paradimethylaminobenzoate, zinc paramethoxycinnamate, zinc lactate, zinc-2-mercaptopyridine-N-oxide complex, zinc gluconate, zinc picrate, zinc citrate, zinc aspartate, zinc naphthenate, zinc salicylate, zinc sebacate, sodium zinc tripolyphosphate, zinc stearate, zinc caprate, zinc laurate, zinc myristate, zinc palmitate, zinc oleate, zinc polyphosphonate, zinc chondroitin-sulfate, zinc undecylenate, zinc ascorbate, zinc pyrithione, hinokitiolato zinc, zinc dipicolinate, zinc-glycerol complex, zinc-bishistidine complex, zinc-3,4-dihydroxybenzoic acid complex, zinc nicotinate, zinc-nicotinamide complex, and other zinc complexes and zinc salts. In the practice of the invention, these zinc compounds may be used either singly or in combination as a mixture of two or more.

Among these zinc compounds, preferable compounds are those containing organic moiety such as zinc stearate, zinc pyrithione, zinc myristate, zinc palmitate and zinc laurate, and those of the inorganic type such as zinc chloride, zinc sulfate and zinc oxide.

In the practice of the invention, at least one member selected from the group consisting of hinokitiol and a salt thereof is (are) used. Examples of the salt of hinokitiol to be used in the practice of the invention are inorganic salts including alkali metal salts such as sodium salt and potassium salt, alkaline earth metal salts such as magnesium salt and other metal salts such as copper salt and zinc salt, and organic salts including alkanolamine salts such as diethanolamine salt, 2-amino-2-ethyl-1,3-propanediol salt and triethanolamine salt, heterocyclic amine salts such as morpholine salt, piperazine salt and piperidine salt, ammonium salt, and basic amino acid salts such as arginine salt, lysine salt and histidine salt. The basic amino acids each may be in the D form or in the L form or in the form of a mixture of these. In the practice of the invention, hinokitiol and salts thereof may be used either singly or two or more of them may be used in combination.

Among these, preferable compounds are hinokitiol and hinokitiol sodium salt.

The proportions of the zinc compound and hinokitiol or a salt thereof to be incorporated into the compositions of the invention are not particularly limited provided that the intended effects of the invention can be produced. Generally, however, it is recommended that both are incorporated in a former:latter weight ratio of about 0.05–99.95:99.95–0.05, preferably about 10–99.95: 90–0.05, and more preferably about 50–99.9:50–0.1. Thus, it is recommended to use the zinc compound in an amount of about 0.05 to 99.95% by weight, preferably about 10 to 99.95% by weight, more preferably about 50 to 99.9% by weight, and to use hinokitiol or a salt thereof in an amount of about 99.95 to 0.05 % by weight, preferably about 90 to 0.05% by weight, more preferably about 50 to 0.1% by weight, based on the total amount of the zinc compound and hinokitiol or the salt thereof.

When the compositions of the invention are to be used as medicaments, the zinc compound and hinokitiol or a salt thereof may be used in a manner such that both of them are contained in a single pharmaceutical preparation. It is also possible to formulate them independently into separate preparations and utilize both of the pharmaceutical preparations. Such preparations are produced by using diluents or excipients that are generally used, including fillers, bulking agents or extenders, binders, humectants, disintegrating agents, surfactants, lubricants and so on. For these pharmaceutical preparations, various forms can be selected depending on the purpose of therapy and, as typical examples thereof, there may be mentioned tablets, pills, powders, solutions, suspensions, emulsions, granules, capsules, suppositories, injections (solutions, suspensions, etc.), oleaginous ointments, emulsion ointments, water-soluble ointments, pastes, plasters, lotions, liniments and other preparations for external use.

When the compositions of the invention are to be used as cosmetics, they can be added as antidandruff agents, antiacne agents, antiperspirants and deodorants, bactericides and/or preservatives to the cosmetics for enabling preservation of the cosmetics, for instance. Said cosmetics may be used in various forms including skin care products such as cleansing preparations, creams, milk lotions, makeup creams, oils, packs or the like; makeup cosmetics such as foundations, lipsticks, cheek rouges, eyeliners, mascaras, eye shadows, manicures, face powders or the like; hair care preparations such as hair dressing preparations, hair tonics, hair colour or the like; oral sanitary preparations such as dentifrice, mouth wash or the like; bath preparations, whitening preparations, sunscreen preparations, acne treatment preparations, etc. These can be produced by the methods that are conventional in the art.

In producing such cosmetics, various known cosmetic base materials, such as vehicles, binders, lubricants, disintegrating agents, etc., can be used as necessary and, further, various oleaginous materials, such as oils, fats, waxes, hydrocarbons, fatty acids, higher alcohols, ester oils, metal soaps, etc., pharmacologically active materials, such as animal or plant extracts, vitamins, hormones, amino acids, etc., surfactants, colors, dyes, pigments, perfumes, preservatives, bactericides, humectants, thickening agents, antioxidants, metal ion sequestering agents and other already known various components or additives can be used as necessary in a suitable combination.

In using the compositions of the invention as medicaments, the active ingredient concentrations are not particularly limited provided that the compositions have the desired effects or benefits. Generally, however, they recommendably contain a zinc compound and hinokitiol or a salt thereof in a total amount of about 0.001 to 20% by weight, preferably about 0.01 to 15% by weight, more preferably about 0.01 to 10% by weight.

The compositions of the invention may be formulated in the form of formulations which are used as diluted with a diluent such as water immediately prior to use. Such formulation to be used as diluted may generally contain a zinc compound and hinokitiol or a salt thereof in a total amount of about 0.001 to 100% by weight, preferably in a total amount of about 0.001 to 50% by weight.

In cases where the compositions of the invention are to be used as cosmetics, the concentration thereof may vary depending on the form and the like, hence cannot be specified in a general manner or are not particularly limited. Generally, however, the compositions recommendably contain a zinc compound and hinokitiol or a salt thereof in a total amount of about 0.0001 to 99.9% by weight, preferably about 0.001 to 30% by weight. The cosmetics mentioned above may be used after further dilution with water, olive oil or some other suitable solvent.

In shaping into the form of tablets, a variety of materials so far well known as carriers or vehicles in this field of art can be used. Thus, for example, use may be made of excipients such as lactose, sucrose, sodium chloride, glucose, urea, starch, calcium carbonate, kaolin, crystalline cellulose, silicic acid, etc., binders such as water, ethanol, propanol, simple syrup, glucose solution, starch solution, gelatin solution, carboxymethylcellulose, shellac, methylcellulose, potassium phosphate, polyvinylpyrrolidone, etc., disintegrating agents such as dried starch, sodium alginate, agar powder, laminaran powder, sodium hydrogen carbonate, calcium carbonate, polyoxyethylenesorbitan fatty acid esters, sodium lauryl sulfate, stearic acid monoglyceride, starch, glucose, etc., disintegration preventing agents such as sucrose, stearin, cacao butter, hydrogenated oils, etc., absorption promoting agents such as quaternary ammonium bases, sodium lauryl sulfate, etc., humectants such as glycerin, starch, etc., adsorbents such as starch, lactose, kaolin, bentonite, colloidal silicic acid, etc., lubricants such as purified talc, stearic acid salts, corn starch, waxes, polyethylene glycol, etc., and so forth. The tablets may further be processed to tablets coated with an ordinary coating film, for example sugar coated tablets, gelatin coated tablets, enteric-film coated tablets, film coated tablets, or double-layered tablets or multilayered tablets.

In shaping into the form of pills, a wide variety of materials so far known as carriers or vehicles in this field of art cab be used. Thus, for example, use may be made of excipients such as glucose, lactose, starch, cacao butter, hardened vegetable oils, kaolin, talc, etc., binders such as gum arabic powder, tragacanth powder, gelatin, ethanol, etc., disintegrating agents such as laminaran, agar, etc., and so forth.

In shaping into the form of suppositories, a wide variety of materials so far known as carriers or vehicles in the art can be used. Thus, for example, there may be mentioned polyethylene glycol, cacao butter, higher alcohols, higher alcohol esters, gelatin, semisynthetic glycerides, and so on.

In preparing injections, the solutions, emulsions and suspensions are sterilized and are preferably isotonic with blood. For producing these forms, all diluents conventionally used in this field can be employed. Thus, for instance, water, ethyl alcohol, macrogols, propylene glycol, ethoxylated isostearyl alcohol, polyoxylated isostearyl alcohol, polyoxyethylene sorbitan fatty acid esters and the like can be used. In this case, sodium chloride, glucose or glycerin may be incorporated into the pharmaceutical preparations in an amount sufficient to give isotonic solutions. Conventional solubilizing agents, buffers, soothing agents and the like may also be added.

In preparing ointments, a wide variety of oleaginous bases so far known in this field can be used. As specific examples, there may be mentioned fats and oils such as peanut oil, sesame oil, soybean oil, safflower oil, avocado oil, sunflower oil, corn oil, rapeseed oil, cottonseed oil, castor oil, camellia oil, coconut oil, olive oil, poppy seed oil, cacao oil, beef tallow, lard, wool oil, etc. (lard being particularly preferred), mineral oils such as vaseline, paraffin, silicone oil, squalane, etc. (white vaseline being particularly preferred), higher fatty acid esters, higher aliphatic alcohols and waxes such as isopropyl myristate, n-butyl myristate, isopropyl linoleate, propyl ricinoleate, isopropyl ricinoleate, isobutyl ricinoleate, heptyl ricinoleate, diethyl sebacate, diisopropyl adipate, cetyl alcohol, stearyl alcohol, bleached beeswax, spermaceti, Japan wax, etc, higher fatty acids such as stearic acid, oleic acid, palmitic acid, etc., mono-, di- and triglyceride mixtures derived from saturated or unsaturated fatty acids containing 12 to 18 carbon atoms (lipophilic glycerin monostearate being particularly preferred), and so on. In the practice of the invention, these bases may be used either singly or in combination as a mixture of two or more.

Conventional additives, for example metal soaps, animal or plant extracts, vitamins, hormones, amino acids or other pharmacologically active substances, surfactants, coloring matters, dyes, pigments, perfumes, ultraviolet absorbers, humectants, thickening agents, antioxidants, metal sequestering agents, pH adjusting agents, etc., may be incorporated, as necessary, into the compositions of the invention.

The compositions of the invention are produced by a conventional method.

The method of administration of the above-mentioned pharmaceutical preparations is not particularly limited but the preparations are administered by a method suitably selected depending on the dosage form, the age, sex and other conditions of the patient, the severity of the disease and other factors. Thus, tablets, pills, solutions, suspensions, emulsions, granules and capsules, for instance, are administered orally. Injections are administered, either as such or in admixture with an ordinary parenteral fluid containing glucose, amino acids or the like, by the intravenous route. If desired, they are administered as such via intramuscular, intradermal, subcutaneous or intraperitoneal route. Suppositories are administered rectally. External preparations are applied to the affected parts.

These pharmaceutical preparations of the present invention are recommendably administered in such an amount that the total amount of the active ingredients, i.e., a zinc compound and hinokitiol or a salt thereof is about 1 to 20 mg/kg body weight per human adult per day, and the preparations are administered in a single dose or two or three divided doses.

In using the compositions of the invention in the field of sterilization for external use, the proportions of a zinc compound and hinokitiol or a salt thereof in the compositions are not particularly limited provided that the compositions produce the desired effects. However, it is recommended that the compositions of the invention contain the zinc compound generally in an amount of about 0.00005 to 99% by weight, preferably about 0.001 to 30% by weight, and hinokitiol or a salt thereof generally in an amount of about 0.00005 to 50% by weight, preferably about 0.001 to 20% by weight. The compositions of the invention may also be diluted for external application, if so desired.

The compositions of the invention for sterilization for external use may contain various additives known in this field in addition to the above-mentioned active ingredients. Examples of such additives are fats and oils such as avocado oil, olive oil, coconut oil, beef tallow, lard, etc.; waxes such as beeswax, spermaceti, lanolin, etc; hydrocarbons such as liquid paraffin, vaseline, squalane, silicone oil, etc.; fatty acids such as lauric acid, myristic acid, palmitic acid, stearic acid, oleic acid, etc.; higher aliphatic alcohols such as cetyl alcohol, stearyl alcohol, 2-hexyldecanol, 2-octyldodecanol, etc.; esters such as isopropyl myristate, 2-octyldodecyl myristate, cetyl iso-octanoate, iso-nonyl iso-nonylate, dinonylpropylene glycol, etc.; mono-, di- and triglycerides of saturated or unsaturated fatty acids containing 8 to 20 carbon atoms such as glycerol monostearate, glycerol monooleate, etc.; lower alcohols such as methanol, ethanol, isopropanol, etc.; polyhydric alcohols such as glycerin, propylene glycol, 1,3-butylene glycol, hexylene glycol, etc.; water; various organic solvents; metal soaps; pharmacologically active materials such as animal or plant extracts, vitamins, hormones, amines, etc.; surfactants, colors, dyes, pigments, perfumes, ultraviolet absorbers, humectants, thickening agents, antioxidants, metal ion sequestering agents, pH adjusting agents, skin astringents, deodorants, bleaches, fluorescent whitening agents, builders, various gases for aerosol, etc.

Conventional means can be used for applying the composition of the present invention to the part to be externally sterilized according to the method of the present invention. Examples of the means include application by spraying, application by brushing, wiping with a cloth, a paper towel or wet tissues, aerosol, etc.

The composition of the present invention can be added to cleaning agents for proprietary and medical supply to be externally sterilized (such as clothes, food, furniture, gauze, sheets, curtains, etc.), to starches, to softeners, to bleaches, etc. The compositions of the invention are also suitably applied to animals and products for animals to be externally sterilized.

The compositions of the invention have excellent antibacterial and antifungal activities and are particularly useful in the treatment of various infectious diseases caused by various bacteria and/or fungi, for example various skin diseases including dermatitis such as atopic dermatitis, nummular dermatitis, autosensitization dermatitis, diaper dermatitis and stasis dermatitis, eczema such as housewives (hand) eczema and dry eczema, pustular psoriasis, burn, redness resulting from burn, impetigo, rash, miliaria, sore, abrasion, secondary infection through scratching, etc.

In addition, the compositions of the invention are very low in skin irritancy and allergy-inducing potential and therefore can be applied not only to babies, infants, children and other patients with skin diseases, for example patients susceptible to skin irritation, but also in the treatment of skin diseases in mammals other than humans (pet animals such as dogs, cats, etc., domestic animals such as cattle, horses, etc., and so on).

The compositions of the invention possess excellent antibacterial and antifungal activities, are safe and very weak in irritancy, and can be suitably used in babies, infants, children and other patients with skin diseases, patients susceptible to irritation and so forth. The compositions of the invention can also be suitably used in patients with atopic dermatitis or contact dermatitis.

The present invention provides a method of sterilization comprising using a composition which has excellent antibacterial and antifungal activities for gram-positive and gram-negative bacteria and which is low in toxicity and very low in side effects. Particularly, the composition of the invention has very strong antibacterial and antifungal activities for gram-positive bacteria such as those belonging to the genera Staphylococcus, Streptococcus, Clostridium, *Corynebacterium diphtheriae*, *Tubercle bacillus* and gram-negative bacteria such as those belonging to the genera Neisseria, Escherichia, Citrobacter, Salmonella, Shigella, Klebsiella and Pseudomonas, anaerobes such as those belonging to the genera Clostridium, Peptococcus, Peptostreptococcus, Propionibacterium and Bacteroides, Zygomycetes including those belonging to the genera Mucor, Ascomycetes including those belonging to the genera Aspergillus and Penicillium, Deuteromycotina including those belonging to the genera Cryptococcus, Candida, Dermatophyte and Pityrosporum, and like fungi.

Furthermore, the method of the present invention produces excellent antibacterial effect against various bacteria and clinical isolates which are resistant to one of the antibiotics such as penicillins, cephems, quinolones, aminoglycosides, macrolides, tetracyclines or like antibiotics. In particular, the method of the invention produces remarkable bactericidal effects against methicillin-resistant *Staphylococcus aureus* (MRSA) and methicillin-resistant *Staphlococcus epidermidis* (MRSE). Furthermore, the method of the invention is efficacious against multiple drug-resistant MRSA and MRSE such as those resistant to quinolone, aminoglycoside, macrolide and tetracycline antibiotics.

The use of a zinc compound in combination with hinokitiol or a salt thereof inhibit the so-called paradoxical effect (i.e., a phenomenon that the antibacterial activity of drugs against bacteria is paradoxically reduced as their concentrations are increased) observed when hinokitiol or a salt thereof is singly used against genus Staphylococcus or the like, and therefore, the bactericidal effects of hinokitiol or a salt thereof is thereby further increased.

The method of controlling bacteria or fungi according to the invention also has a feature of being highly safe and being excellent in absorptive property and excretive property. More specifically, according to the method of the invention, high renal excretion and parapedesis occur.

The method of external sterilization is advantageously applicable for washing off and disinfecting wet tissues, chemical clothes, paper towels, moist hand towels, carpets, floors, tableware, general clothing, general instruments (such as furniture and glasses), medical clothing, etc., for removing bacteria from dishwashers, drainpipes, etc. and for washing and removing bacteria from medical instruments (such as gauze, optical lenses, etc.), beverage containers, products for animals, etc.

EXAMPLES

The following production examples and test examples are further illustrative of the present invention. Hereinafter, "%" means "% by weight".

Production Example 1 (Zinc oxide ointment)

| | |
|---|---|
| Hinokitiol | 0.5 g |
| Lard | 300.0 g |
| Bleached beeswax | 60.0 g |
| Zinc oxide | 100.0 g |
| White petrolatum | q.s. |
| Total | 1000.0 g |

(1) Hinokitiol was weighed, and a portion of lard was added thereto, and the mixture was heated to about 40° C. and stirred to give a homogeneous melt. (2) The remaining portion of lard, bleached beeswax and white petrolatum were dissolved on a water bath and stirred to give a mixture at 80° C. (3) Zinc oxide was weighed into a mortar. Thereto was added portionwise the mixture prepared in the above-mentioned step (2) with stirring to give a homogenous mixture, which was then cooled to about 40° C. with stirring. (4) Then, the mixture prepared in the above step (1) was added at about 40° C. and stirring was continued until solidification to give the desired zinc oxide ointment.

Production Example 2 (Zinc oxide ointment)

| | |
|---|---|
| Hinokitiol | 0.1 g |
| Olive oil | 100.0 g |
| Zinc oxide | 100.0 g |
| Simple ointment (Japanese Pharmacopoeia) | q.s. |
| Total | 1000.0 g |

(1) Hinokitiol was weighed. To this was added a portion of olive oil. The mixture was heated to about 40° C. and stirred to give a homogeneous melt. (2) The remaining portion of olive oil and simple ointment (Japanese Pharmacopoeia) were dissolved on a water bath and then stirred to give a mixture at 80° C. (3) Zinc oxide was weighed into a mortar. Thereto was added portionwise with stirring the mixture prepared in the above step (2) to give a homogenous mixture, which was then cooled to about 40° C. with stirring. (4) Then, the mixture prepared in the above step (1) was added at about 40° C., followed by stirring well until solidification to give the desired zinc oxide ointment.

Production Example 3 (Absorptive zinc oxide ointment)

|  |  |
|---|---|
| Lipophilic glycerin monostearate | 50.0 g |
| Zinc oxide | 50.0 g |
| White petrolatum | q.s. |
| Hinokitiol sodium salt | 0.05 g |
| Glycerin | 30.0 g |
| Purified water | 50.0 g |
| Total | 1000.0 g |

(1) Hinokitiol sodium salt, glycerin and purified water were heated to about 60° C. and stirred to give a homogeneous melt. (2) Lipophilic glycerin monostearate and white petrolatum were dissolved on a water bath and then stirred to give a mixture at 60° C. (3) The mixture prepared in the above step (1) was added portionwise to the mixture prepared in the above step (2) with uniform stirring. The whole mixture was then cooled to about 40° C. with stirring. (4) Zinc oxide was weighed into a mortar. Thereto was added portionwise the mixture prepared in the above step (3), followed by thorough stirring until solidification to give the desired zinc oxide ointment.

|  |  |
|---|---|
| Stearic acid | 10.0% |
| Paraffin wax (135F) | 2.0% |
| Spermaceti | 2.0% |
| Cetyl alcohol | 2.0% |
| Cetyl isooctanoate | 5.0% |
| Polyoxyethylenesorbitan (20EO) monolaurate | 3.0% |
| Zinc acetate | 0.015% |
| Sodium hydroxide | 0.15% |
| Concentrated glycerin | 5.0% |
| Hinokitiol | 0.02% |
| Perfume | suitable amount |
| Purified water | Balance |
| Total | 100.0% |

(1) Stearic acid, paraffin wax (135F), spermaceti, cetyl alcohol, cetyl isooctanoate and polyoxyethylenesorbitan (20EO) monolaurate were heated to 80°–85° C. to give a homogeneous melt. (2) Zinc acetate, sodium hydroxide, concentrated glycerin and purified water were heated to 80–°85° C. and stirred to give a homogeneous mixture. (3) At 80° C., the mixture prepared in the above step (2) was added portionwise to the mixture prepared in the above step (1) and, after uniform emulsification, the whole mixture was cooled to 45° C. with stirring. (4) At 45° C., hinokitiol and perfume were added to the mixture prepared in the above step (3), and the mixture was stirred to homogeneity and cooled to room temperature with stirring to give the desired vanishing cream. Said vanishing cream was in the form of a stable emulsion.

Production Example 5 (Cleansing cream)

|  |  |
|---|---|
| Bleached beeswax | 3.0% |
| Liquid paraffin | 30.0% |
| Cetyl alcohol | 2.0% |
| Cetyl isooctanoate | 10.0% |
| Triethanolamine | 0.2% |
| Propylene glycol | 5.0% |
| Zinc acetate | 0.1% |
| Antioxidant | suitable amount |
| Hinokitiol | 0.05% |
| Perfume | suitable amount |
| Purified water | Balance |
| Total | 100.0% |

The above ingredients were admixed for emulsification following the procedure of Production Example 4 to give a stable emulsion.

Production Example 6 (Milk lotion)

|  |  |
|---|---|
| Stearic acid | 3.0 |
| Spermaceti | 3.0% |
| Lipophilic glycerin monostearate | 2.0% |
| Bleached beeswax | 2.0% |
| Saturated fatty acid ($C_8$–$C_{12}$) triglyceride | 10.0% |
| L-Arginine | 1.0% |
| Sorbitol | 3.0% |
| Zinc pyrithione | 0.02% |
| Hinokitiol | 0.02% |
| Perfume | 0.1% |
| Purified water | Balance |
| Total | 100.0% |

The above ingredients were admixed for emulsification following the procedure of Production Example 4, whereupon a stable emulsion was obtained.

|  |  |
|---|---|
| Ethyl alcohol | 10.0% |
| Polyoxyethylene (9EO) lauryl ether | 2.0% |
| Kankoh SO 201 | 0.001% |
| Perfume | suitable amount |
| Concentrated glycerin | 5.0% |
| 1,3-Butylene glycol | 3.0% |
| Hinokitiolato zinc | 0.05% |
| Hinokitiol | 0.05% |
| Color | suitable amount |
| Purified water | Balance |
| Total | 100.0% |

(1) Polyoxyethylene (9EO) lauryl ether, Kankoh SO 201 and perfume were added to and uniformly dissolved in ethyl alcohol. (2) Concentrated glycerin, 1,3-butylene glycol and hinokitiolato zinc were added to and uniformly dissolved in purified water. (3) At 80° C., the mixture prepared in the above step (2) was added to the mixture prepared in the above step (1) and, after uniform stirring for solubilization, hinokitiol was added and color was further added for coloration to give a lotion.

Production Example 8 (Zinc oxide ointment)

|  |  |
|---|---|
| Lard | 20.95% |
| Bleached beeswax | 7.0% |
| Lipophilic glycerin monostearate | 2.0% |
| White petrolatum | 60.0% |
| Zinc oxide | 10.0% |

-continued

| | |
|---|---|
| Hinokitiol | 0.05% |
| Total | 100.0% |

(1) Hinokitiol was weighed. To this was added a portion of lard and the mixture was heated to about 40° C. and stirred to give a homogeneous melt. (2) The remaining portion of lard, lipophilic glycerin monostearate, bleached beeswax and white petrolatum were dissolved on a water bath and stirred to give a mixture at 80° C. (3) Zinc oxide was weighed into a mortar. To this was added portionwise the mixture prepared in the above step (2) with uniform stirring. The resulting mixture was cooled to about 40° C. with stirring. (4) Then, the mixture prepared in the above step (1) was added at about 40° C. The whole mixture was stirred well until solidification to give the desired zinc oxide ointment.

Test Example 1 (Antibacterial activity test)

The drugs tested were hinokitiol SP (Takasago Perfumery Co., Ltd.; Lot 112108) and zinc oxide (Wako Pure Chemical Industries, Ltd.; Lot 71620). The test bacterial strain used was *Staphylococcus epidermidis* KPU1. (Staphylococcus epidermidis).

Cells of the above test strain precultured on SCD slant medium (18 to 20 hours, 37° C.) were suspended in SCD medium and the suspension was diluted and adjusted to $10^6$ to $10^7$ cells/ml and allowed to stand for several tens of minutes. This cell suspension was added to drug solutions which had been adjusted to predetermined drug concentrations. Then, shaking culture was performed (diluent: SCDLP medium or sterile physiological saline; medium: SCDLP agar medium; incubation temperature: 37° C.; incubation period: 24 to 48 hours) and viable cells were counted at timed intervals.

The concentrations of drugs for testing and the method of preparing the drugs were as follows. Thus, a control was prepared by adding 9 ml of the cell suspension to 1 ml of sterile distilled water. Hinokitiol (0.02%) was prepared by diluting an alcohol solution containing hinokitiol at a concentration of 5% with sterile distilled water to give a 0.2% hinokitiol solution and adding 9 ml of the cell suspension to 1 ml of said 0.2% solution. Hinokitiol (0.04%) was prepared by diluting an alcohol solution containing hinokitiol at a concentration of 5% with sterile distilled water to give a 0.4% hinokitiol solution and adding 9 ml of the cell suspension to 1 ml of said 0.4% solution. Zinc oxide (0.1%) was prepared by adding 10 ml of the cell suspension to 0.01 g of zinc oxide (ZnO). Hinokitiol (0.04%)+zinc oxide (0.1%) was prepared by adding 1 ml of the 0.4% hinokitiol solution to 0.01 g of zinc oxide, followed by addition of 9 ml of the cell suspension. Zinc acetate (0.4%) was prepared by adding 10 ml of the cell suspension to 0.04 g of zinc acetate ($Zn(CH_3COO)_2 \cdot 2H_2O$). Hinokitiol (0.02%)+zinc acetate (0.4%) was prepared by adding 1 ml of the 0.2% hinokitiol solution to 0.04 g of zinc acetate, followed by addition of 9 ml of the cell suspension.

Viable cells were counted at timed intervals. The results obtained are shown in FIG. 1 and FIG. 2.

Figure 2:
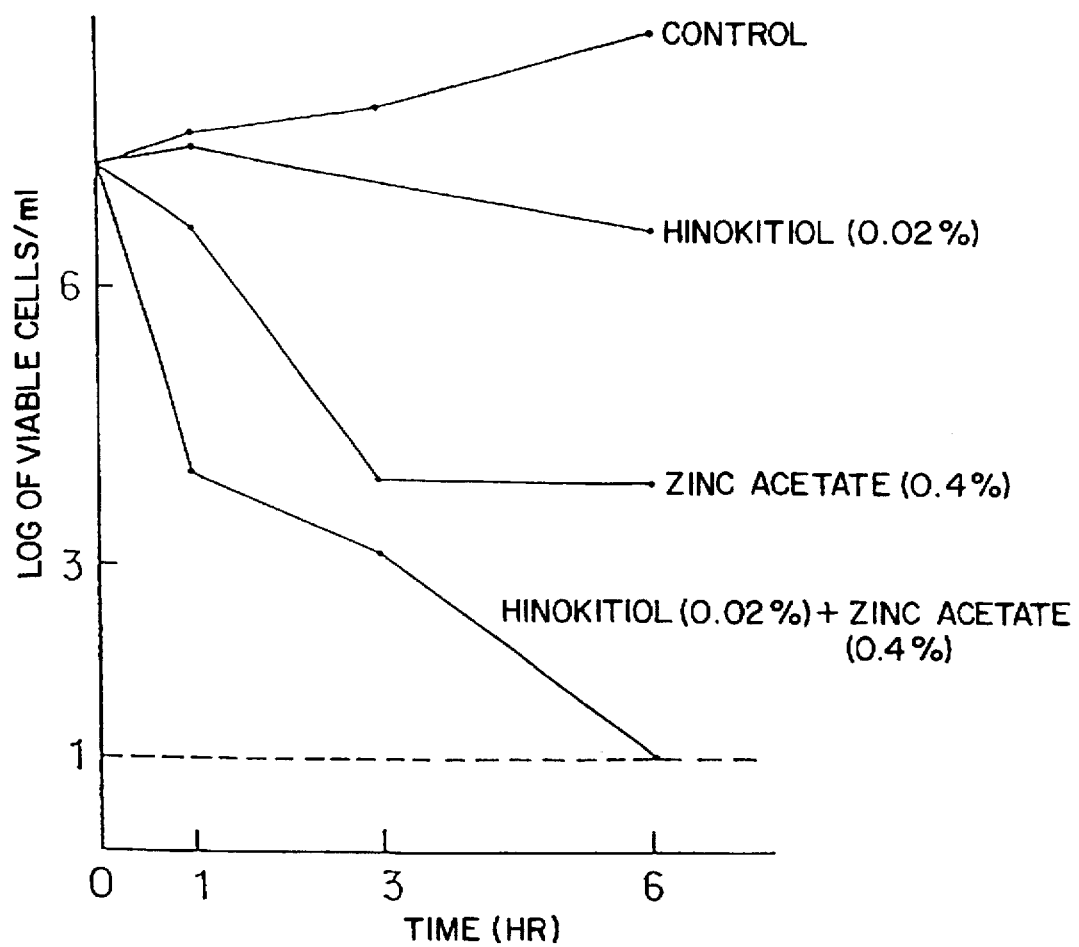

From FIG. 1 and FIG. 2, which are graphs showing the change in the number of viable cells counted with time, it is apparent that the use of hinokitiol in combination with zinc oxide or zinc acetate results in markedly increased antibacterial activity.

Test Example 2 (Antibacterial activity test)

The effects of the combined use of hinokitiol and zinc acetate were examined by the checkerboard dilution method.

Hinokitiol SP and zinc acetate (Wako Pure Chemical Industries, Ltd.; Lot LKR 3395) were used as the test drugs. The following six bacterial strains were used as the test microorganisms.

Bacterial strains used:

*Staphylococcus* (S.) *aureus* 209 PJC

S. *aureus* ATCC 6538 (Staphylococcus aureus)

S. *epidermidis* KPU1 (Staphylococcus epidermidis)

*Escherichia coli* K-12 (Escherichia coli)

*Escherichia coli* ATCC 8739 (Escherichia coli)

*Bacillus subtilis* IAM 1213 (Bacillus subtilis)

Each strain was precultured in Mueller-Hinton medium (incubation temperature: 37° C.; incubation period: 18 to 20 hours), and the culture was diluted with Mueller-Hinton medium to $10^8$ cells/ml or $10^6$ cells/ml and the dilutions were used as the test bacterial cell suspensions.

The concentrations of the drug for testing and the method of preparing the drugs were as follows. Thus, an alcohol solution containing hinokitiol at a concentration of 5% was diluted with sterile distilled water to give a 0.4% hinokitiol solution. This solution was serially double-diluted with sterile distilled water to give solutions containing hinokitiol at concentrations of 2000 µg/ml, 1000 µg/ml, 500 µg/ml, 250 µg/ml, 125 µg/ml, 62.5 µg/ml, 31.3 µg/ml and 15.6 µg/ml. Separately, an aqueous solution containing zinc acetate at a concentration of 3.2% was serially double-diluted with sterile distilled water to give aqueous solution containing zinc acetate at concentrations of 16000 µg/ml, 8000 µg/ml, 4000 µg/ml, 2000 µg/ml, 1000 µg/ml, 500 µg/ml and 250 µg/ml.

When hinokitiol and zinc acetate were to be used combinedly, 0.5 ml each of the above two drug solutions containing respectively 20 times concentrations used were added, together with 9 ml of the medium, to each petri dish to obtain an agar plate. When hinokitiol and zinc acetate were to be used each individually, 1 ml of a 10-fold concentrated hinokitiol or zinc acetate solution and 9 ml of the medium were added to each petri dish to obtain an agar plate.

Mueller-Hinton plate media containing hinokitiol and/or zinc acetate at various concentrations were prepared by the above method and inoculated with each cell suspension with a cell concentration of $10^8$ cells/ml or $10^6$ cells/ml and, after incubating at 37° C. for 48 hours, judgment was made as to whether cells had grown or not. The results obtained are shown in Table 1 through Table 12. In the following tables, "+" means that growth was observed, "−" means that no growth was observed, and "±" means that very slight growth was observed.

TABLE 1

Bacterial strain used: *Staphylococcus aureus* 209PJC
Inoculum size: $10^8$ cells/ml (Unit: µg/ml)

| Hinokitiol | Zinc acetate | | | | | | | |
|---|---|---|---|---|---|---|---|---|
| | 1600 | 800 | 400 | 200 | 100 | 50 | 25 | 0 |
| 200 | − | − | − | − | − | − | − | − |
| 100 | − | − | − | − | − | − | − | ± |
| 50 | − | − | − | − | − | − | − | + |
| 25 | − | − | − | − | − | − | − | + |
| 12.5 | − | − | − | − | − | − | + | + |
| 6.25 | − | − | − | − | − | − | + | + |
| 3.13 | − | − | − | − | − | + | + | + |
| 1.56 | − | − | − | − | + | + | + | + |
| 0 | − | − | + | + | + | + | + | |

TABLE 2

Bacterial strain used: *Staphylococcus aureus* 209PJC
Inoculum size: $10^6$ cells/ml (Unit: μg/ml)

| Hinokitiol | Zinc acetate | | | | | | | |
|---|---|---|---|---|---|---|---|---|
| | 1600 | 800 | 400 | 200 | 100 | 50 | 25 | 0 |
| 200 | − | − | − | − | − | − | − | − |
| 100 | − | − | − | − | − | − | − | + |
| 50 | − | − | − | − | − | − | − | + |
| 25 | − | − | − | − | − | − | − | + |
| 12.5 | − | − | − | − | − | − | − | + |
| 6.25 | − | − | − | − | − | − | − | − |
| 3.13 | − | − | − | − | − | − | − | − |
| 1.56 | − | − | − | − | − | − | − | − |
| 0 | − | − | + | + | + | + | + | |

TABLE 3

Bacterial strain used: *Staphylococcus aureus* ATCC 6538
Inoculum size: $10^8$ cells/ml (Unit: μg/ml)

| Hinokitiol | Zinc acetate | | | | | | | |
|---|---|---|---|---|---|---|---|---|
| | 1600 | 800 | 400 | 200 | 100 | 50 | 25 | 0 |
| 200 | − | − | − | − | − | − | − | − |
| 100 | − | − | − | − | − | − | − | + |
| 50 | − | − | − | − | − | − | − | + |
| 25 | − | − | − | − | − | − | − | + |
| 12.5 | − | − | − | − | − | − | + | + |
| 6.25 | − | − | − | − | − | − | − | − |
| 3.13 | − | − | − | − | − | − | − | − |
| 1.56 | − | − | − | − | + | − | − | − |
| 0 | − | − | + | + | + | + | + | |

TABLE 4

Bacterial strain used: *Staphylococcus aureus* ATCC 6538
Inoculum size: $10^6$ cells/ml (Unit: μg/ml)

| Hinokitiol | Zinc acetate | | | | | | | |
|---|---|---|---|---|---|---|---|---|
| | 1600 | 800 | 400 | 200 | 100 | 50 | 25 | 0 |
| 200 | − | − | − | − | − | − | − | − |
| 100 | − | − | − | − | − | − | − | − |
| 50 | − | − | − | − | − | − | − | + |
| 25 | − | − | − | − | − | − | − | + |
| 12.5 | − | − | − | − | − | − | ± | + |
| 6.25 | − | − | − | − | − | − | − | − |
| 3.13 | − | − | − | − | − | − | − | − |
| 1.56 | − | − | − | − | − | − | − | − |
| 0 | − | − | ± | + | + | + | + | |

TABLE 5

Bacterial strain used: *Staphylococcus epidermidis* KPU 1
Inoculum size: $10^8$ cells/ml (Unit: μg/ml)

| Hinokitiol | Zinc acetate | | | | | | | |
|---|---|---|---|---|---|---|---|---|
| | 1600 | 800 | 400 | 200 | 100 | 50 | 25 | 0 |
| 200 | − | − | − | − | − | − | − | − |
| 100 | − | − | − | − | − | − | − | + |
| 50 | − | − | − | − | − | − | − | + |
| 25 | − | − | − | − | − | − | − | + |

TABLE 5-continued

Bacterial strain used: *Staphylococcus epidermidis* KPU 1
Inoculum size: $10^8$ cells/ml (Unit: μg/ml)

| Hinokitiol | Zinc acetate | | | | | | | |
|---|---|---|---|---|---|---|---|---|
| | 1600 | 800 | 400 | 200 | 100 | 50 | 25 | 0 |
| 12.5 | − | − | − | − | − | − | + | + |
| 6.25 | − | − | − | − | − | − | − | − |
| 3.13 | − | − | − | − | − | − | − | − |
| 1.56 | − | − | − | − | − | − | − | − |
| 0 | − | − | + | + | + | + | + | |

TABLE 6

Bacterial strain used: *Staphylococcus epidermidis* KPU 1
Inoculum size: $10^6$ cells/ml (Unit: μg/ml)

| Hinokitiol | Zinc acetate | | | | | | | |
|---|---|---|---|---|---|---|---|---|
| | 1600 | 800 | 400 | 200 | 100 | 50 | 25 | 0 |
| 200 | − | − | − | − | − | − | − | − |
| 100 | − | − | − | − | − | − | − | + |
| 50 | − | − | − | − | − | − | − | + |
| 25 | − | − | − | − | − | − | − | + |
| 12.5 | − | − | − | − | − | − | − | + |
| 6.25 | − | − | − | − | − | − | − | − |
| 3.13 | − | − | − | − | − | − | − | − |
| 1.56 | − | − | − | − | − | − | − | − |
| 0 | − | − | + | + | + | + | + | |

TABLE 7

Bacterial strain used: *Escherichia coli* K-12
Inoculum size: $10^8$ cells/ml (Unit: μg/ml)

| Hinokitiol | Zinc acetate | | | | | | | |
|---|---|---|---|---|---|---|---|---|
| | 1600 | 800 | 400 | 200 | 100 | 50 | 25 | 0 |
| 200 | − | − | − | − | − | − | − | − |
| 100 | − | − | − | − | − | − | − | − |
| 50 | − | − | − | − | − | − | − | − |
| 25 | − | − | − | − | − | − | − | − |
| 12.5 | − | − | − | − | − | − | − | + |
| 6.25 | − | − | − | + | + | + | + | + |
| 3.13 | − | − | − | + | + | + | + | + |
| 1.56 | − | − | + | + | + | + | + | + |
| 0 | − | − | + | + | + | + | + | |

TABLE 8

Bacterial strain used: *Escherichia coli* K-12
Inoculum size: $10^6$ cells/ml (Unit: μg/ml)

| Hinokitiol | Zinc acetate | | | | | | | |
|---|---|---|---|---|---|---|---|---|
| | 1600 | 800 | 400 | 200 | 100 | 50 | 25 | 0 |
| 200 | − | − | − | − | − | − | − | − |
| 100 | − | − | − | − | − | − | − | − |
| 50 | − | − | − | − | − | − | − | − |
| 25 | − | − | − | − | − | − | − | + |
| 12.5 | − | − | − | − | − | − | − | + |
| 6.25 | − | − | − | + | + | + | + | + |
| 3.13 | − | − | + | + | + | + | + | |

TABLE 8-continued

Bacterial strain used: *Escherichia coli* K-12
Inoculum size: $10^6$ cells/ml (Unit: μg/ml)

| Hinokitiol | Zinc acetate | | | | | | | |
|---|---|---|---|---|---|---|---|---|
| | 1600 | 800 | 400 | 200 | 100 | 50 | 25 | 0 |
| 1.56 | − | − | + | + | + | + | + | + |
| 0 | − | − | + | + | + | + | + | |

TABLE 9

Bacterial strain used: *Escherichia coli* ATCC 8739
Inoculum size: $10^8$ cells/ml (Unit: μg/ml)

| Hinokitiol | Zinc acetate | | | | | | | |
|---|---|---|---|---|---|---|---|---|
| | 1600 | 800 | 400 | 200 | 100 | 50 | 25 | 0 |
| 200 | − | − | − | − | − | − | − | − |
| 100 | − | − | − | − | − | − | − | − |
| 50 | − | − | − | − | − | − | − | − |
| 25 | − | − | − | − | − | − | − | + |
| 12.5 | − | − | − | − | − | − | − | + |
| 6.25 | − | − | − | − | + | + | + | + |
| 3.13 | − | − | − | + | + | + | + | + |
| 1.56 | − | − | − | + | + | + | + | + |
| 0 | − | − | + | + | + | + | + | |

TABLE 10

Bacterial strain used: *Escherichia coli* ATCC 8739
Inoculum size: $10^6$ cells/ml (Unit: μg/ml)

| Hinokitiol | Zinc acetate | | | | | | | |
|---|---|---|---|---|---|---|---|---|
| | 1600 | 800 | 400 | 200 | 100 | 50 | 25 | 0 |
| 200 | − | − | − | − | − | − | − | − |
| 100 | − | − | − | − | − | − | − | − |
| 50 | − | − | − | − | − | − | − | − |
| 25 | − | − | − | − | − | − | − | + |
| 12.5 | − | − | − | − | − | − | − | + |
| 6.25 | − | − | − | − | + | + | + | + |
| 3.13 | − | − | − | − | + | + | + | + |
| 1.56 | − | − | − | + | + | + | + | + |
| 0 | − | − | − | + | + | + | + | |

TABLE 11

Bacterial strain used: *Bacillus subtilis* IAM 1213
Inoculum size: $10^8$ cells/ml (Unit: μg/ml)

| Hinokitiol | Zinc acetate | | | | | | | |
|---|---|---|---|---|---|---|---|---|
| | 1600 | 800 | 400 | 200 | 100 | 50 | 25 | 0 |
| 200 | − | − | − | − | − | − | − | − |
| 100 | − | − | − | − | − | − | − | − |
| 50 | − | − | − | − | − | − | − | + |

TABLE 11-continued

Bacterial strain used: *Bacillus subtilis* IAM 1213
Inoculum size: $10^8$ cells/ml (Unit: μg/ml)

| Hinokitiol | Zinc acetate | | | | | | | |
|---|---|---|---|---|---|---|---|---|
| | 1600 | 800 | 400 | 200 | 100 | 50 | 25 | 0 |
| 25 | − | − | − | − | − | − | − | + |
| 12.5 | − | − | − | − | − | − | − | + |
| 6.25 | − | − | − | − | − | − | + | + |
| 3.13 | − | − | − | − | − | − | − | + |
| 1.56 | − | − | − | − | − | + | + | + |
| 0 | − | − | + | + | + | + | + | |

TABLE 12

Bacterial strain used: *Bacillus subtilis* IAM 1213
Inoculum size: $10^6$ cells/ml (Unit: μg/ml)

| Hinokitiol | Zinc acetate | | | | | | | |
|---|---|---|---|---|---|---|---|---|
| | 1600 | 800 | 400 | 200 | 100 | 50 | 25 | 0 |
| 200 | − | − | − | − | − | − | − | − |
| 100 | − | − | − | − | − | − | − | − |
| 50 | − | − | − | − | − | − | − | + |
| 25 | − | − | − | − | − | − | − | + |
| 12.5 | − | − | − | − | − | − | − | + |
| 6.25 | − | − | − | − | − | − | − | + |
| 3.13 | − | − | − | − | − | − | − | + |
| 1.56 | − | − | − | − | − | − | + | + |
| 0 | − | − | − | + | + | + | + | |

From Tables 1 to 12 shown above, it is apparent that the combined use of hinokitiol and zinc acetate results in markedly improved antibacterial activity.

Test Example 3 (Antibacterial activity test)

The effects of the combined use of hinokitiol and zinc chloride were examined after 24 hours of incubation at 37° C. in the same manner as in Test Example 2 (except that the medium alone was changed, namely, Trypto Soy Bouillon medium was used as the preculture medium, dried bouillon medium for dilution, and heart infusion agar medium for plate preparation).

Hinokitiol SP and zinc chloride (Wako Pure Chemical Industries, Ltd.; Lot TWQ 1277) were used as the test drugs, and the following three bacterial strains as the test organisms.

Strains used:

*Staphylococcus aureus* 209PJC
*Bacillus subtilis* PCI 219
*Micrococcus luteus* ATCC 9341

The results obtained are shown below in Table 13 through Table 15.

TABLE 13

Bacterial strain used: *Staphylococcus aureus* 209PJC
Inoculum size: $10^6$ cells/ml (Unit: µg/ml)

| | | Zinc chloride | | | | | | | | | |
|---|---|---|---|---|---|---|---|---|---|---|---|
| | | 400 | 200 | 100 | 50 | 25 | 12.5 | 6.25 | 3.13 | 1.56 | 0.78 | 0 |
| Hinokitiol | 100 | − | − | − | − | − | − | − | − | − | − | − |
| | 50 | − | − | − | − | − | − | − | − | − | − | − |
| | 25 | − | − | − | − | − | − | − | + | + | + | + |
| | 12.5 | − | − | − | − | − | + | + | + | + | + | + |
| | 6.25 | − | − | − | − | − | − | − | − | − | − | − |
| | 3.13 | − | − | − | − | − | − | − | − | − | − | − |
| | 1.56 | − | − | − | − | − | − | − | − | − | − | − |
| | 0.78 | − | − | + | + | + | + | + | + | + | + | + |
| | 0.39 | − | − | + | + | + | + | + | + | + | + | + |
| | 0.20 | − | − | + | + | + | + | + | + | + | + | + |
| | 0 | − | − | + | + | + | + | + | + | + | + | |

TABLE 14

Bacterial strain used: *Bacillus subtilis* PCI 219
Inoculum size: $10^6$ cells/ml (Unit: µg/ml)

| | | Zinc chloride | | | | | | | | | |
|---|---|---|---|---|---|---|---|---|---|---|---|
| | | 400 | 200 | 100 | 50 | 25 | 12.5 | 6.25 | 3.13 | 1.56 | 0.78 | 0 |
| Hinokitiol | 100 | − | − | − | − | − | − | − | − | − | − | − |
| | 50 | − | − | − | − | − | − | − | − | − | − | − |
| | 25 | − | − | − | − | − | − | − | − | − | − | − |
| | 12.5 | − | − | − | − | − | − | + | + | + | + | + |
| | 6.25 | − | − | − | − | − | − | + | + | + | + | + |
| | 3.13 | − | − | − | − | − | − | + | + | + | + | + |
| | 1.56 | − | − | − | − | + | + | + | + | + | + | + |
| | 9.78 | − | + | + | + | + | + | + | + | + | + | + |
| | 0.39 | − | − | + | + | + | + | + | + | + | + | + |
| | 0.20 | − | − | + | + | + | + | + | + | + | + | + |
| | 0 | − | − | + | + | + | + | + | + | + | + | |

TABLE 15

Bacterial strain used: *Micrococcus luteus* ATCC 9341
Inoculum size: $10^6$ cells/ml (Unit: µg/ml)

| | | Zinc chloride | | | | | | | | | |
|---|---|---|---|---|---|---|---|---|---|---|---|
| | | 400 | 200 | 100 | 50 | 25 | 12.5 | 6.25 | 3.13 | 1.56 | 0.78 | 0 |
| Hinokitiol | 100 | − | − | − | − | − | − | − | − | − | − | − |
| | 50 | − | − | − | − | − | − | − | − | − | − | − |
| | 25 | − | − | − | − | − | − | − | − | − | − | + |
| | 12.5 | − | − | − | − | − | + | + | + | + | + | + |
| | 6.25 | − | − | − | − | + | + | + | + | + | + | + |
| | 3.13 | − | − | − | − | + | + | + | + | + | + | + |
| | 1.56 | − | − | + | + | + | + | + | + | + | + | + |
| | 0.78 | − | + | + | + | + | + | + | + | + | + | + |
| | 0.39 | − | + | + | + | + | + | + | + | + | + | + |
| | 0.20 | − | + | + | + | + | + | + | + | + | + | + |
| | 0 | − | + | + | + | + | + | + | + | + | + | |

Test Example 4 (Antibacterial activity test)

The effects of the combined use of hinokitiol and zinc dipicolinate were investigated after 24 hours of incubation at 37° C. in the same manner as in Test Example 2 (except that the medium alone was changed, namely Trypto Soy Bouillon medium was used as the preculture medium, dried bouillon medium for dilution, and heart infusion agar medium for plate preparation).

Hinokitiol SP and zinc dipicolinate were used as the test drugs and the following two bacterial strains as the test organisms.

Strains used:

*Staphylococcus epidermidis* KPU-1
Bacillus subtilisATCC 6633

The results obtained are shown below in Table 16 and Table 17.

TABLE 16

Bacterial strain used: *Staphylococcus epidermides* KPU-1
Inoculum size: $10^6$ cells/ml

| | | Zinc dipicolinate | | | | | | | | | | (Unit: μg/ml) |
|---|---|---|---|---|---|---|---|---|---|---|---|---|
| | | 400 | 200 | 100 | 50 | 25 | 12.5 | 6.25 | 3.13 | 1.56 | 0.78 | 0 |
| Hinokitiol | 100 | − | − | − | − | − | − | − | − | − | − | − |
| | 50 | − | − | − | − | − | − | − | − | − | + | − |
| | 25 | − | − | − | − | − | + | + | + | + | + | + |
| | 12.5 | − | − | − | − | − | − | + | + | + | + | + |
| | 6.25 | − | − | − | − | − | − | − | − | − | − | − |
| | 3.13 | − | − | − | − | − | − | − | − | − | − | − |
| | 1.56 | − | − | − | − | − | − | − | − | − | − | − |
| | 0.78 | − | − | − | − | − | − | − | − | − | − | − |
| | 0.39 | − | − | − | − | − | − | − | − | − | − | − |
| | 0.20 | − | + | + | + | + | + | + | + | + | + | + |
| | 0 | + | + | + | + | + | + | + | + | + | + | |

TABLE 17

Bacterial strain used: *Bacillus subtilis* ATCC 6633
Inoculum size: $10^6$ cells/ml

| | | Zinc dipicolinate | | | | | | | | | | (Unit: μg/ml) |
|---|---|---|---|---|---|---|---|---|---|---|---|---|
| | | 400 | 200 | 100 | 50 | 25 | 12.5 | 6.25 | 3.13 | 1.56 | 0.78 | 0 |
| Hinokitiol | 100 | − | − | − | − | − | − | − | − | − | − | − |
| | 50 | − | − | − | − | − | − | − | − | − | − | − |
| | 25 | − | − | − | − | − | − | − | − | + | + | + |
| | 12.5 | − | − | − | − | − | + | + | + | + | + | + |
| | 6.25 | − | − | − | − | − | + | + | + | + | + | + |
| | 3.13 | − | − | − | − | + | + | + | + | + | + | + |
| | 1.56 | − | − | + | + | + | + | + | + | + | + | + |
| | 0.78 | − | − | − | + | + | + | + | + | + | + | + |
| | 0.39 | − | + | + | + | + | + | + | + | + | + | + |
| | 0.20 | − | + | + | + | + | + | + | + | + | + | + |
| | 0 | − | + | + | + | + | + | + | + | + | + | |

Test Example 5 (Antibacterial activity test)

The effects of the combined use of hinokitiol and zinc compound shown below were examined after 24 hours of incubation at 37° C. in the same manner as in Test Example 3 (except that the medium alone was changed, namely, Trypto Soy Bouillon medium was used as the preculture medium, dried bouillon medium for dilution, and heart infusion agar medium for plate preparation).

Hinokitiol tested were hinokitiol SP (Takasago Perfumery Co., Ltd.; Lot No. 11208).

The zinc compound tested were as follows.

1) Zinc sulfate heptahydrate (Wako Pure Chemical Industries, Co., Ltd.; Lot No. PTN 2472)

2) Zinc undecylenate (Maruishi Seiyaku Kabushiki Kaisha; Lot No. 2304)

3) Zinc pyrithione solution ("Tomisaido Z-50", Toyama Kagaku Kabushiki Kaisha; Lot No. Y974)

4) Zinc stearate (Mitsuwa Kagaku Yakuhin Kabushiki Kaisha; Lot No. 47837)

5) Zinc palmitate (Mitsuwa Kagaku Yakuhin Kabushiki Kaisha; Lot No. 45328)

6) Zinc myristate (Mitsuwa Kagaku Yakuhin Kabushiki Kaisha; Lot No. 46763)

7) Zinc laurate (Mitsuwa Kagaku Yakuhin Kabushiki Kaisha; Lot No. 47140)

8) Zinc salicylate trihydrate (Wako Pure Chemical Industries, Co., Ltd.; Lot No. WDL 1860)

9) Zinc lactate trihydrate (Wako Pure Chemical Industries, Co., Ltd.; Lot No. LKG 1661)

10) Zinc phosphate tetrahydrate (Wako Pure Chemical Industries, Co., Ltd.; Lot No. WDR 2680)

11) Zinc nitrate hexahydrate (Wako Pure Chemical Industries, Co., Ltd.; Lot No. TWJ 1858)

12) Zinc nicotinate

13) Zinc-nicotinamide complex

14) Zinc-3,4-dihydroxybenzoic acid complex

15) Zinc-bishistidine complex

Zinc nicotinate, zinc-nicotinamide complex, zinc-3,4-dihydroxybenzoic acid complex and zinc-bishistidine complex mentioned above are all known compounds, and in this test these compounds used were those synthesized following the procedure of Preparation Examples 1-4 to be described below.

The test bacterial strain used was *Staphylococcus aureus* 209 PJC (Inoculum size: $10^6$ cells/ml).

The concentrations of the drugs for testing and the method of preparing the drugs were as follows.

An alcohol (ethanol) solution containing hinokitiol at a concentration of 5.0% was diluted with sterile distilled water to give a 0.4% hinokitiol solution. This solution was serially double-diluted with sterile distilled water to give solution containing hinokitiol at concentrations of 2000 µg/ml, 1000 µg/ml, 500 µg/ml, 250 µg/ml, 125 µg/ml, 62.5 µg/ml, 31.3 µg/ml, 15.6 µg/ml, 7.8 µg/ml, 3.9 µg/ml (and optionally 2.0 µg/ml).

In the case of zinc nitrate hexahydrate and zinc salicylate trihydrate, an aqueous solution containing said zinc compound at a concentration of 6.4% was serially double-diluted with sterile distilled water to give solutions containing said zinc compound at concentrations of 32000 µg/ml, 16000 µg/ml, 8000 µg/ml, 4000 µg/ml, 2000 µg/ml, 1000 µg/ml, 500 µg/ml, 250 µg/ml, 125 µg/ml and 62.5 µg/ml.

In the case of zinc sulfate heptahydrate, an aqueous solution containing this zinc compound at a concentration of 3.2% was serially double-diluted with sterile distilled water to give solutions containing said zinc compound at concentrations of 16000 µg/ml, 8000 µg/ml, 4000 µg/ml, 2000 µg/ml, 1000 µg/ml, 500 µg/ml, 250 µg/ml, 125 µg/ml, 62.5 µg/ml and 31.3 µg/ml.

In the case of zinc nicotinamide complex, an aqueous solution containing said zinc compound at a concentration of 1.6% was serially double-diluted with sterile distilled water to give solutions containing said zinc compound at concentrations of 8000 µg/ml, 4000 µg/ml, 2000 µg/ml, 1000 µg/ml, 500 µg/ml, 250 µg/ml, 125 µg/ml, 62.5 µg/ml, 31.3 µg/ml and 15.6 µg/ml.

In the case of zinc myristate, zinc stearate, zinc palmitate, zinc undecylenate and zinc laurate, a dispersion of said zinc compound in ethanol having a concentration of 6.4% was serially double-diluted with ethanol to give dispersions containing said zinc compound at concentrations of 32000 µg/ml, 16000 µg/ml, 8000 µg/ml, 4000 µg/ml, 2000 µg/ml, 1000 µg/ml, 500 µg/ml, 250 µg/ml, 125 µg/ml and 62.5 µg/ml.

In the case of zinc phosphate tetrahydrate, zinc lactate trihydrate and zinc nicotinate, a dispersion of said zinc compound in sterile distilled water having a concentration of 6.4% was serially double-diluted with sterile distilled water to give dispersions containing said zinc compound at concentrations of 32000 µg/ml, 16000 µg/ml, 8000 µg/ml, 4000 µg/ml 2000 µg/ml, 1000 µg/ml, 500 µg/ml, 250 µg/ml, 125 µg/ml and 62.5 µg/ml.

In the case of zinc pyrithione, a dispersion of zinc pyrithione in sterile distilled water having a concentration of 0.1% was serially double-diluted with sterile distilled water to give dispersions containing zinc pyrithione at concentrations of 500 µg/ml, 250 µg/ml, 125 µg/ml, 62.5 µg/ml, 31.3 µg/ml, 15.6 µg/ml, 7.8 µg/ml, 3.9 µg/ml, 2.0 µg/ml and 1.0 µg/ml.

In the case of zinc-3,4-dihydroxybenzoic acid complex and zinc-bishistidine complex, a dispersion containing said zinc compound in sterile distilled water at a concentration of 3.2% was serially double-diluted with sterile distilled water to give dispersions containing said zinc compound at concentrations of 16000 µg/ml, 8000 µg/ml, 4000 µg/ml, 2000 µg/ml, 1000 µg/ml, 500 µg/ml, 250 µg/ml, 125 µg/ml 62.5 µg/ml and 31.3 µg/ml.

The results obtained are shown below in Table 18 through 32. From the results obtained by the use of various concentrations of hinokitiol and various concentrations of zinc compound, it is seen that the antibacterial effect obtained by the combined use is greater than or equal to the sum of the effects obtained by the use of each drug alone. This shows that the use of hinokitiol in combination with the zinc compound remarkably improves or improves the antibacterial activity.

TABLE 18

Bacterial strain used: *Staphylococcus aureus* 209PJC
Inoculum size: $10^6$ cells/ml (Unit: µg/ml)

| | | $ZnSO_4.7H_2O$ | | | | | | | | | | |
|---|---|---|---|---|---|---|---|---|---|---|---|---|
| | | 1600 | 800 | 400 | 200 | 100 | 50 | 25 | 12.5 | 6.25 | 3.13 | 0 |
| Hinokitiol | 200 | − | − | − | − | − | − | − | − | − | − | − |
| | 100 | − | − | − | − | − | − | − | − | − | − | − |
| | 50 | − | − | − | − | − | − | − | − | − | + | + |
| | 25 | − | − | − | − | − | + | + | + | + | + | + |
| | 12.5 | − | − | − | − | − | − | − | − | − | − | − |
| | 6.25 | − | − | − | − | − | − | − | − | − | − | − |
| | 3.13 | − | − | − | − | − | − | − | − | − | − | − |
| | 1.56 | − | − | − | + | + | + | + | + | + | + | + |
| | 0.78 | − | − | − | + | + | + | + | + | + | + | + |
| | 0.39 | − | − | − | + | + | + | + | + | + | + | + |
| | 0.20 | − | − | − | + | + | + | + | + | + | + | + |
| | 0 | − | − | ± | + | + | + | + | + | + | + | |

TABLE 19

Bacterial strain used: *Staphylococcus aureus* 209PJC
Inoculum size: 10⁶ cells/ml (Unit: µg/ml)

|  |  | Zinc pyrithione | | | | | | | | | | |
|---|---|---|---|---|---|---|---|---|---|---|---|---|
|  |  | 50 | 25 | 12.5 | 6.25 | 3.13 | 1.56 | 0.78 | 0.39 | 0.20 | 0.10 | 0 |
| Hinokitiol | 200 | − | − | − | − | − | − | − | − | − | − | − |
|  | 100 | − | − | − | − | − | − | − | − | − | − | − |
|  | 50 | − | − | − | − | − | − | + | + | + | + | + |
|  | 25 | − | − | − | − | + | + | + | + | + | + | + |
|  | 12.5 | − | − | − | − | − | − | − | − | − | − | − |
|  | 6.25 | − | − | − | − | − | − | − | − | − | − | − |
|  | 3.13 | − | − | − | − | − | − | − | − | − | − | − |
|  | 1.56 | − | − | − | − | − | − | − | − | − | − | − |
|  | 0.78 | − | − | − | − | − | − | + | + | + | + | + |
|  | 0.39 | − | − | − | − | − | + | + | + | + | + | + |
|  | 0.20 | − | − | − | − | − | + | + | + | + | + | + |
|  | 0 | − | − | − | − | − | + | + | + | + | + |  |

TABLE 20

Bacterial strain used: *Staphylococcus aureus* 209PJC
Inoculum size: 10⁶ cells/ml (Unit: µg/ml)

|  |  | Zinc laurate | | | | | | | | | | |
|---|---|---|---|---|---|---|---|---|---|---|---|---|
|  |  | 3200 | 1600 | 800 | 400 | 200 | 100 | 50 | 25 | 12.5 | 6.25 | 0 |
| Hinokitiol | 200 | − | − | − | − | − | − | − | − | − | − | − |
|  | 100 | − | − | − | − | − | − | − | − | − | − | − |
|  | 50 | − | − | − | − | − | − | − | − | − | − | + |
|  | 25 | − | − | − | − | − | − | − | + | + | + | + |
|  | 12.5 | − | − | − | − | − | − | − | − | − | − | − |
|  | 6.25 | − | − | − | − | − | − | − | − | − | − | − |
|  | 3.13 | − | − | − | − | − | − | − | − | − | − | − |
|  | 1.56 | − | − | − | − | − | − | − | − | − | + | + |
|  | 0.78 | + | + | + | + | + | + | + | + | + | + | + |
|  | 0.39 | + | + | + | + | + | + | + | + | + | + | + |
|  | 0.20 | + | + | + | + | + | + | + | + | + | + | + |
|  | 0 | − | − | − | − | − | − | + | + | + | + |  |

TABLE 21

Bacterial strain used: *Staphylococcus aureus* 209PJC
Inoculum size: 10⁶ cells/ml (Unit: µg/ml)

|  |  | Zinc myristate | | | | | | | | | | |
|---|---|---|---|---|---|---|---|---|---|---|---|---|
|  |  | 3200 | 1600 | 800 | 400 | 200 | 100 | 50 | 25 | 12.5 | 6.25 | 0 |
| Hinokitiol | 200 | − | − | − | − | − | − | − | − | − | − | − |
|  | 100 | − | − | − | − | − | − | − | − | − | − | − |
|  | 50 | − | − | − | − | − | − | − | − | − | − | ± |
|  | 25 | − | − | − | − | − | − | − | − | − | − | + |
|  | 12.5 | − | − | − | − | − | − | − | − | − | − | − |
|  | 6.25 | − | − | − | − | − | − | − | − | − | − | − |
|  | 3.13 | − | − | − | − | − | − | − | − | − | − | − |
|  | 1.56 | − | − | − | − | − | − | − | − | − | − | − |
|  | 0.78 | − | − | − | − | − | − | − | + | + | + | + |
|  | 0.39 | − | − | − | + | + | + | + | + | + | + | + |
|  | 0 | − | − | − | + | + | + | + | + | + | + |  |

TABLE 22

Bacterial strain used: *Staphylococcus aureus* 209PJC
Inoculum size: 10⁶ cells/ml (Unit: μg/ml)

| | | Zinc stearate | | | | | | | | | | |
|---|---|---|---|---|---|---|---|---|---|---|---|---|
| | | 3200 | 1600 | 800 | 400 | 200 | 100 | 50 | 25 | 12.5 | 6.25 | 0 |
| Hinokitiol | 200 | − | − | − | − | − | − | − | − | − | − | − |
| | 100 | − | − | − | − | − | − | − | − | − | − | − |
| | 50 | − | − | − | − | − | − | − | − | − | − | ± |
| | 25 | − | − | − | − | − | − | − | ± | + | + | + |
| | 12.5 | − | − | − | − | − | − | − | − | − | − | − |
| | 6.25 | − | − | − | − | − | − | − | − | − | − | − |
| | 3.13 | − | − | − | − | − | − | − | − | − | − | − |
| | 1.56 | − | − | − | − | − | − | − | − | − | − | − |
| | 0.78 | − | − | − | − | − | − | + | + | + | + | + |
| | 0.39 | − | − | ± | + | + | + | + | + | + | + | + |
| | 0 | − | − | − | − | ± | + | + | + | + | + | |

TABLE 23

Bacterial strain used: *Staphylococcus aureus* 209PJC
Inoculum size: 10⁶ cells/ml (Unit: μg/ml)

| | | Zinc palmitate | | | | | | | | | | |
|---|---|---|---|---|---|---|---|---|---|---|---|---|
| | | 3200 | 1600 | 800 | 400 | 200 | 100 | 50 | 25 | 12.5 | 6.25 | 0 |
| Hinokitiol | 200 | − | − | − | − | − | − | − | − | − | − | − |
| | 100 | − | − | − | − | − | − | − | − | − | − | − |
| | 50 | − | − | − | − | − | − | − | − | − | − | ± |
| | 25 | − | − | − | − | − | − | − | ± | + | + | + |
| | 12.5 | − | − | − | − | − | − | − | − | − | + | − |
| | 6.25 | − | − | − | − | − | − | − | − | − | − | − |
| | 3.13 | − | − | − | − | − | − | − | − | − | − | − |
| | 1.56 | − | − | − | − | − | − | − | − | − | − | − |
| | 0.78 | + | + | + | + | + | + | + | + | + | + | + |
| | 0.39 | + | + | + | + | + | + | + | + | + | + | + |
| | 0 | ± | ± | ± | ± | + | + | + | + | + | + | |

TABLE 24

Bacterial strain used: *Staphylococcus aureus* 209PJC
Inoculum size: 10⁶ cells/ml (Unit: μg/ml)

| | | Zinc undecylenate | | | | | | | | | | |
|---|---|---|---|---|---|---|---|---|---|---|---|---|
| | | 3200 | 1600 | 800 | 400 | 200 | 100 | 50 | 25 | 12.5 | 6.25 | 0 |
| Hinokitiol | 200 | − | − | − | − | − | − | − | − | − | − | − |
| | 100 | − | − | − | − | − | − | − | − | − | − | − |
| | 50 | − | − | − | − | − | − | − | ± | − | − | ± |
| | 25 | − | − | − | − | − | − | − | ± | + | + | + |
| | 12.5 | − | − | − | − | − | − | − | − | − | − | − |
| | 6.25 | − | − | − | − | − | − | − | − | − | − | − |
| | 3.13 | − | − | − | − | − | − | − | − | − | − | − |
| | 1.56 | − | − | − | − | − | − | − | − | − | − | − |
| | 0.78 | − | − | − | − | − | − | + | + | + | + | + |
| | 0.39 | − | − | − | − | + | + | + | + | + | + | + |
| | 0 | − | − | − | − | + | + | + | + | + | + | |

TABLE 25

Bacterial strain used: *Staphylococcus aureus* 209PJC
Inoculum size: $10^6$ cells/ml (Unit: μg/ml)

Zinc phosphate tetrahydrate

| | | 3200 | 1600 | 800 | 400 | 200 | 100 | 50 | 25 | 12.5 | 6.25 | 0 |
|---|---|---|---|---|---|---|---|---|---|---|---|---|
| Hinokitiol | 200 | − | − | − | − | − | − | − | − | − | − | − |
| | 100 | − | − | − | − | − | − | − | − | − | − | − |
| | 50 | − | − | − | − | − | − | − | − | − | − | ± |
| | 25 | − | − | − | − | − | − | + | + | + | + | + |
| | 12.5 | − | − | − | − | − | − | − | − | − | − | − |
| | 6.25 | − | − | − | − | − | − | − | − | − | − | − |
| | 3.13 | − | − | − | − | − | − | − | − | − | − | − |
| | 1.56 | − | − | − | − | − | − | − | − | − | − | − |
| | 0.78 | + | + | + | + | + | + | + | + | + | + | + |
| | 0.39 | + | + | + | + | + | + | + | + | + | + | + |
| | 0 | + | + | + | + | + | + | + | + | + | + | |

TABLE 26

Bacterial strain used: *Staphylococcus aureus* 209PJC
Inoculum size: $10^6$ cells/ml
(Unit: μg/ml)

Zinc salicylate trihydrate

| | | 3200 | 1600 | 800 | 400 | 200 | 100 | 50 | 25 | 12.5 | 6.25 | 0 |
|---|---|---|---|---|---|---|---|---|---|---|---|---|
| Hinoki- | 200 | − | − | − | − | − | − | − | − | − | − | − |
| tiol | 100 | − | − | − | − | − | − | − | − | − | − | − |
| | 50 | − | − | − | − | − | − | − | − | − | − | + |
| | 25 | − | − | − | − | − | − | − | − | + | + | + |
| | 12.5 | − | − | − | − | − | − | − | − | − | − | + |
| | 6.25 | − | − | − | − | − | − | − | − | − | − | − |
| | 3.13 | − | − | − | − | − | − | − | − | − | − | − |
| | 1.56 | − | − | − | − | − | − | − | − | − | − | − |
| | 0.78 | − | − | − | + | + | + | + | + | + | + | + |
| | 0.39 | − | − | − | + | + | + | + | + | + | + | + |
| | 0 | − | − | − | + | + | + | + | + | + | + | |

TABLE 27

Bacterial strain used: *Staphylococcus aureus* 209PJC
Inoculum size: $10^6$ cells/ml
(Unit: μg/ml)

Zinc lactate trihydrate

| | | 3200 | 1600 | 800 | 400 | 200 | 100 | 50 | 25 | 12.5 | 6.25 | 0 |
|---|---|---|---|---|---|---|---|---|---|---|---|---|
| Hinoki- | 200 | − | − | − | − | − | − | − | − | − | − | − |
| tiol | 100 | − | − | − | − | − | − | − | − | − | − | − |
| | 50 | − | − | − | − | − | − | − | − | − | − | + |
| | 25 | − | − | − | − | − | − | − | − | + | + | + |
| | 12.5 | − | − | − | − | − | − | − | − | − | − | + |
| | 6.25 | − | − | − | − | − | − | − | − | − | − | − |
| | 3.13 | − | − | − | − | − | − | − | − | − | − | − |
| | 1.56 | − | − | − | − | − | − | − | − | − | − | − |
| | 0.78 | − | − | − | − | + | + | + | + | + | + | + |
| | 0.39 | − | − | − | − | + | + | + | + | + | + | + |
| | 0 | − | − | − | + | + | + | + | + | + | + | |

TABLE 28

Bacterial strain used: *Staphylococcus aureus* 209PJC
Inoculum size: $10^6$ cells/ml
(Unit: μg/ml)

| | | Zinc nitrate hexahydrate | | | | | | | | | | |
|---|---|---|---|---|---|---|---|---|---|---|---|---|
| | | 3200 | 1600 | 800 | 400 | 200 | 100 | 50 | 25 | 12.5 | 6.25 | 0 |
| Hinoki-tiol | 200 | − | − | − | − | − | − | − | − | − | − | − |
| | 100 | − | − | − | − | − | − | − | − | − | − | − |
| | 50 | − | − | − | − | − | − | − | − | − | − | + |
| | 25 | − | − | − | − | − | − | − | − | + | + | + |
| | 12.5 | − | − | − | − | − | − | − | − | − | + | + |
| | 6.25 | − | − | − | − | − | − | − | − | − | − | − |
| | 3.13 | − | − | − | − | − | − | − | − | − | − | − |
| | 1.56 | − | − | − | − | − | − | − | − | − | − | − |
| | 0.78 | − | − | − | − | + | + | + | + | + | + | + |
| | 0.39 | − | − | − | − | + | + | + | + | + | + | + |
| | 0 | − | − | − | ± | + | + | + | + | + | + | |

TABLE 29

Bacterial strain used: *Staphylococcus aureus* 209PJC
Inoculum size: $10^6$ cells/ml
(Unit: μg/ml)

| | | Zinc nicotinamide complex | | | | | | | | | |
|---|---|---|---|---|---|---|---|---|---|---|---|
| | | 800 | 400 | 200 | 100 | 50 | 25 | 12.5 | 6.25 | 3.13 | 1.56 | 0 |
| Hinoki-tiol | 200 | − | − | − | − | − | − | − | − | − | − | − |
| | 100 | − | − | − | − | − | − | − | − | − | − | − |
| | 50 | − | − | − | − | − | − | − | − | ± | + | + |
| | 25 | − | − | − | − | − | − | + | + | + | + | + |
| | 12.5 | − | − | − | − | − | − | ± | − | − | − | + |
| | 6.25 | − | − | − | − | − | − | − | − | − | − | − |
| | 3.13 | − | − | − | − | − | − | − | − | − | − | − |
| | 1.56 | − | − | − | − | − | − | − | − | − | − | − |
| | 0.78 | − | + | + | + | + | + | + | + | + | + | − |
| | 0.39 | − | + | + | + | + | + | + | + | + | + | + |
| | 0 | − | + | + | + | + | + | + | + | + | + | |

TABLE 30

Bacterial strain used: *Staphylococcus aureus* 209PJC
Inoculum size: $10^6$ cells/ml
(Unit: μg/ml)

| | | Zinc nicotinate | | | | | | | | | | |
|---|---|---|---|---|---|---|---|---|---|---|---|---|
| | | 3200 | 1600 | 800 | 400 | 200 | 100 | 50 | 25 | 12.5 | 6.25 | 0 |
| Hinoki-tiol | 200 | − | − | − | − | − | − | − | − | − | − | − |
| | 100 | − | − | − | − | − | − | − | − | − | − | − |
| | 50 | − | − | − | − | − | − | − | − | − | − | + |
| | 25 | − | − | − | − | − | − | − | + | + | + | + |
| | 12.5 | − | − | − | − | − | − | − | − | + | + | + |
| | 6.25 | − | − | − | − | − | − | − | − | − | − | − |
| | 3.13 | − | − | − | − | − | − | − | − | − | − | − |
| | 1.56 | − | − | − | − | − | − | − | − | − | − | − |
| | 0.78 | − | − | + | + | + | + | + | + | + | + | − |
| | 0.39 | − | − | + | + | + | + | + | + | + | + | + |
| | 0 | − | − | + | + | + | + | + | + | + | | |

TABLE 31

Bacterial strain used: *Staphylococcus aureus* 209PJC
Inoculum size: $10^6$ cells/ml
(Unit: μg/ml)

| | | Zinc-3,4-dihydroxybenzoic acid complex | | | | | | | | | |
|---|---|---|---|---|---|---|---|---|---|---|---|
| | | 1600 | 800 | 400 | 200 | 100 | 50 | 25 | 12.5 | 6.25 | 3.13 | 0 |
| Hinoki-tiol | 200 | − | − | − | − | − | − | − | − | − | − | − |
| | 100 | − | − | − | − | − | − | − | − | − | − | − |
| | 50 | − | − | − | − | − | − | − | − | + | + | + |
| | 25 | − | − | − | − | − | − | − | + | + | + | + |
| | 12.5 | − | − | − | − | − | + | + | + | − | − | − |
| | 6.25 | − | − | − | + | + | − | − | − | − | − | − |
| | 3.13 | − | − | − | + | + | + | − | − | − | − | − |
| | 1.56 | − | + | + | + | + | + | + | + | + | − | − |
| | 0.78 | + | + | + | + | + | + | + | + | + | + | + |
| | 0.39 | + | + | + | + | + | + | + | + | + | + | + |
| | 0 | + | + | + | + | + | + | + | + | + | + | |

TABLE 32

Bacterial strain used: *Staphylococcus aureus* 209PJC
Inoculum size: $10^6$ cells/ml
(Unit: μg/ml)

| | | Zinc-bishistidine complex | | | | | | | | | |
|---|---|---|---|---|---|---|---|---|---|---|---|
| | | 1600 | 800 | 400 | 200 | 100 | 50 | 25 | 12.5 | 6.25 | 3.13 | 0 |
| Hinoki-tiol | 200 | − | − | − | − | − | − | − | − | − | − | − |
| | 100 | − | − | − | − | − | − | − | − | − | − | − |
| | 50 | − | − | − | − | − | − | − | − | − | − | − |
| | 25 | − | − | − | − | − | − | − | − | − | + | + |
| | 12.5 | − | − | − | − | − | − | + | + | + | + | + |
| | 6.25 | − | − | − | − | − | − | − | − | − | − | − |
| | 3.13 | − | − | − | − | − | − | − | − | − | − | − |
| | 1.56 | − | − | + | + | + | + | − | − | − | − | − |
| | 0.78 | ± | + | + | + | + | + | + | + | + | + | + |
| | 0.39 | + | + | + | + | + | + | + | + | + | + | + |
| | 0 | + | + | + | + | + | + | + | + | + | + | |

Preparation Example 1:

Zinc nicotinate:

The reagents used were of guaranteed grade nicotinic acid (Kanto Chem. Co., Inc.), Zinc acetate.2H₂O and ammonia water (Wako Pure Chem. Industries Ltd.)

5.0 g of nicotinic acid was dissolved in 100 ml of deionized water with stirring in a hot bath. Similarly, 4.5 g of zinc acetate.2H₂O was dissolved in 100 ml of deionized water in a hot bath and both were mixed with vigorous stirring. Subsequently, ammonia water (1:1 mixture of 25% ammonia water and distilled water) was added to adjust the pH to 8.5. The mixture was heated in a hot bath of about 80° C. for 10 minutes to complete the reaction, was continuously heated to concentrate the mixture, then being evaporated to about 20 ml. After cooling in a refrigerator, the precipitate was filtered with a No. 5B paper filter, and washed with deionized water. The obtained material was dissolved with heating in 200 ml of deionized water, followed by concentration to 20 ml. The concentrate was cooled down at room temperature, and washed three times with deionized water. The obtained material was dried sufficiently at 65° C. or lower temperature in an electric oven to obtain 3.0 g of zinc nicotinate (hereinafter abbreviated as Compound A).

Crystal form: White powder or white plates

Elemental analysis: Experimental (%): C 45.60 H 2.83 N 8.92 Zn 21.16

The above experimental values agreed with the following calculated ratio:

Nicotinic acid: Zinc: $H_2O$=2:1:0

NMR spectrum: NMR spectrum was measured using an apparatus, JNM-GSX270 (manufactured by Nihon Denshi): Solid $^{13}$C-NMR δ ppm; 172.5 (C=O) 150.1 (C-6,2) 139.7 (C-4) 132.5 (C-3) 125.5 (c-5)

IR spectrum:

Nicotinic acid (starting material):

2200–3000 cm$^{-1}$ m (COOH stretching vibration)

1730 s (C=O stretching vibration of carboxylic acid)

1419 m (C—O—H deformation vibration)

1330, 1305 s (C—O stretching vibration)

Zinc nicotinate (Compound A):

2700–3600 cm$^{-1}$ m (O—H stretching vibration)

1638(1600–1650) s (COO⁻, anion of carboxylic acid, antisymmetric vibration)

1416(1360–1450) s (COO⁻, anion of carboxylic acid, symmetric vibration)

From the above data, nicotinic acid is suggested to have a free carboxyl group, that is, it is not a dimer, whereas Compound A is considered to be a carboxylate.

Moreover, from the IR spectrum of wave number 200 to 400 cm$^{-1}$, it was considered that the peak in the vicinity of 220 cm$^{-1}$ was attributed to the bond of zinc and nitrogen, and therefore, it was presumed that nicotinic acid and zinc were bonded by way of the ionic bonding or coordinate bonding.

Preparation Example 2

Zinc-bishistidine complex:

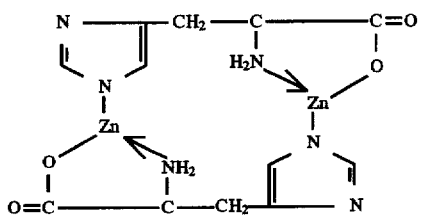

L-Histidine, zinc sulfate.7H$_2$O and sodium hydrogencarbonate were guaranteed grade of Wako Pure Chem. Industries Ltd., all of which were used without further purification.

7.4 g of zinc sulfate.7H$_2$O was dissolved in 60 ml of deionized water with stirring in a water bath. To this solution was added 6.4 g of sodium hydrogencarbonate with vigorous stirring. The reaction was allowed to complete by heating the mixture at 80° C. for 10 minutes to produce zinc carbonate. With further vigorous stirring, 8.0 g of L-histidine was added to this solution, and the reaction was allowed to complete by heating the mixture at 80° C. for 10 minutes. The mixture was there evaporated to about 30 ml, and then cooled down at room temperature. The precipitated complexes were filtrated with a No. 5C filter paper, followed by washing with 50 ml of water and decanting. The supernatant was removed with a capillary. The crystals were washed with 200 ml of deionized water in a water bath, decanted and the supernatant was removed, and this procedure was repeated three times for purification. The obtained material was dried sufficiently at 65° C. or lower temperature in an electric oven to obtain 5.6 g of zinc-bishistidine complex [i.e., zinc(II) bis(L-histidinolato)].

Preparation Example 3

Zinc-3,4-dihydroxybenzic acid complex

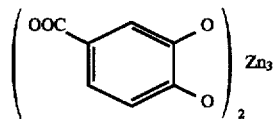

3,4-Dihydroxybenzoic acid (protocatechuic acid) was provided by Tokyo Kasei Kogyo Co., Ltd., and zinc acetate.2H$_2$O, methanol and sodium hydroxide were of guaranteed grade of Wako Pure Chem. Industries Ltd., all of which were used without further purification.

7.0 g of zinc acetate.2H$_2$O was dissolved in 40 ml of deionized water with stirring in a hot water bath. Similarly, 5.0 g of protocatechuic acid was dissolved in 10 ml of methanol in a water bath, to which 20 ml of deionized water was added. Both were vigorously stirred and mixed. Subsequently, a NaOH solution (diluted to 0.25 mol/l) was added adjusting the pH to 5.5 (by the use of a pH meter). The reaction was allowed to complete by heating the mixture in a water bath at about 80° C. for 10 minutes. The mixture was there evaporated to about 20 ml, then cooled down with ice. The precipitated complexes were filtrated with a No. 5C filter paper, followed by washing with deionized water. A procedure of washing and filtrating with 200 ml of deionized water and methanol was repeated three times to purify the product. The obtained product was dried sufficiently at 65° C. or lower temperatures in an electric oven to obtain 4.0 g of zinc-3,4-dihydroxybenzoic acid complex [i.e., bis(3,4-dihydroxybenzoato)zinc(II)].

Preparation Example 4

Zinc-nicotinamide complex:

4.89 g (0.04 mol) of nicotinamide is dissolved in 100 ml of ethanol, to which 2.73 g (0.02 mol) of ZnCl$_2$ in 50 ml of ethanol is added and mixed. When stirred, white crystals immediately precipitate. The precipitate is filtered with a No. 5C filter paper, followed by washing with ethanol and then with diethyl ether. The washed product is allowed to stand for evaporating diethyl ether, and dried at 60° C. in an electric oven to obtain the desired compound.

Elemental analysis:

Calculated (%): C: 37.87 H: 3.18 N: 14.72 Zn: 17.18
Experimental (%): C: 37.41 H: 3.18 N: 14.42 Zn 18.62

The above experimental values agreed with the following calculated ratio:

Nicotinamide: Zinc=2:1

IR spectrum:

Nicotinamide (starting material):

3200–3500 cm$^{-1}$ s (NH stretching vibration based on —CO—NH$_2$—)

1683 s (C=O stretching vibration)

1623 m (—N—H deformation vibration)

Nicotinamide zinc

3200–3500 cm$^{-1}$ s (NH stretching vibration based on —CO—NH$_2$—)

1683 s (C=O stretching vibration)

1608 m (—N—H deformation vibration)

From the above data, nicotinamide zinc has a broader NH stretching vibration based on —CO—NH$_2$ at 3200–3500 cm$^{-1}$ than nicotinamide, and further, since the N—H deformation vibration of the pyridine ring at the vicinity of 1650 cm$^{-1}$ is somewhat varied, it was presumed that nicotinamide and zinc were bonded via a coordinate bonding.

UV spectrum: The product was dissolved in ethanol and the UV spectrum was measured.

| Nicotinamide (starting material): | | | |
|---|---|---|---|
| Peak | | Valley | |
| λ | Absorption | λ | Absorption |
| 262.4 | 0.715 | 245.8 | 0.549 |
| 217.6 | 1.779 | | |
| Zinc nicotinamide | | | |
| Peak | | Valley | |
| λ | Absorption | λ | Absorption |
| 262.6 | 0.498 | 246.4 | 0.380 |
| 216.4 | 1.407 | | |

Test Example 6 (Antibacterial activity test)

The effects of the combined use of hinokitiol and zinc compound shown below were examined after 24 hours of incubation at 37° C. in the same manner as in Test Example 3 (except that the medium alone was changed, namely, Trypto Soy Bouillon medium was used as the preculture medium, dried bouillon medium for dilution, and heart infusion agar medium for plate preparation).

Hinokitiol tested were hinokitiol SP (Takasago Perfumery Co., Ltd.; Lot No. 11208).

The zinc compound tested were as follows.

1) Zinc chloride (Nakaraitesuku Kabushiki Kaisha; Lot No. M3B 1104)

2) Zinc oxide (Sumitomo Cement Kabushiki Kaisha; Lot No. 93-4115)

3) Zinc sulfate heptahydrate (Wako Pure Chemical Industries, Co., Ltd.; Lot No. PTN 2472)

The test bacterial strains used were as follows:

1) Methicillin-resistant *Staphylococcus aureus* MRSA-1

2) Methicillin-resistant *Staphylococcus aureus* MRSA-2

3) Methicillin-resistant *Staphylococcus aureus* MRSA-3

4) Methicillin-resistant *Staphylococcus epidermidis* MRSE-1

The methicillin-resistant Staphylococcus aureus strains MRSA-1, MRSA-2 and MRSA-3 are clinical isolates, and, in addition to resistance to methicillin, have resistance to Ofloxacin (quinolone), Gentamicin sulfate (aminoglycoside), Erythromycin (macrolide) and Minocycline hydrochloride (tetracycline) as shown by the results of MIC (minimum inhibitory concentration) below.

| | Result of MIC | | |
|---|---|---|---|
| | MRSA-1 | MRSA-2 | MRSA-3 |
| Sodium methicillin | <100 | <100 | <100 |
| Ofloxacin | 12.5 | 12.5 | 50 |
| Gentamicin sulfate | <100 | <100 | <100 |
| Erthromycin | <100 | <100 | <100 |
| Minocycline hydrochloride | 25 | 25 | 25 |

Unit: µg/ml

With respect to MRSE-1, the result of MIC of sodium methicillin is shown below.

| strain | Sodium methicillin (µg/ml) |
|---|---|
| MRSE-1 | 100 |

The above MIC values were determined according to the method described in CHEMOTHERAPY VOL. 29; 76–79, 1981.

The method of preparing the drugs was as follows.

An alcohol (ethanol) solution containing hinokitiol at a concentration of 5.0% was diluted with sterile distilled water to give a 0.4% hinokitiol solution and this solution was serially double-diluted with sterile distilled water to give solution containing hinokitiol at concentrations of 2000 µg/ml, 1000 µg/ml, 500 µg/ml, 250 µg/ml, 125 µg/ml, 62.5 µg/ml, 31.3 µg/ml, 15.6 µg/ml, 7.8 µg/ml, 3.9 µg/ml and 2.0 µg/ml.

An aqueous solution containing zinc chloride at a concentration of 1.6% was serially double-diluted with sterile distilled water to give solution containing zinc chloride at concentrations of 8000 µg/ml, 4000 µg/ml, 2000 µg/ml, 1000 µg/ml, 500 µg/ml, 250 µg/ml, 125 µg/ml, 62.5 µg/ml, 31.3 µg/ml and 15.6 µg/ml.

An aqueous dispersion of zinc oxide having a concentration of 1.6% was serially double-diluted with sterile distilled water to give dispersions containing zinc oxide at concentrations of 8000 µg/ml, 4000 µg/ml, 2000 µg/ml, 1000 µg/ml, 500 µg/ml, 250 µg/ml, 125 µg/ml, 62.5 µg/ml, 31.3 µg/ml and 15.6 µg/ml.

An aqueous solution containing zinc sulfate at a concentration of 3.2% was serially double-diluted with sterile distilled water to give solutions containing zinc sulfate at concentrations of 16000 µg/ml, 8000 µg/ml, 4000 µg/ml, 2000 µg/ml, 1000 µg/ml, 500 µg/ml, 250 µg/ml, 125 µg/ml, 62.5 µg/ml and 31.3 µg/ml.

The results obtained are shown in Tables 33–38. From the results obtained by the use of various concentrations of hinokitiol and various concentrations of zinc compound, it is seen that the antibacterial effect obtained by the combined use is greater than or equal to the sum of the effects obtained by the use of each drug alone. This shows that the use of hinokitiol in combination with said zinc compound remarkably improves or improves the antibacterial activity.

TABLE 33

Bacterial strain used: MRSA-1
Inoculum size: $10^6$ cells/ml
(Unit: µg/ml)

| | | Zinc chloride | | | | | | | | | | |
|---|---|---|---|---|---|---|---|---|---|---|---|---|
| | | 800 | 400 | 200 | 100 | 50 | 25 | 12.5 | 6.25 | 3.13 | 1.56 | 0 |
| Hinoki- | 200 | − | − | − | − | − | − | − | − | − | − | − |
| tiol | 100 | − | − | − | − | − | − | − | − | − | − | − |
| | 50 | − | − | − | − | − | − | − | − | − | + | + |
| | 25 | − | − | − | − | − | − | + | + | + | + | + |
| | 12.5 | − | − | − | − | − | − | − | − | − | − | − |
| | 6.25 | − | − | − | − | − | − | − | − | − | − | − |
| | 3.13 | − | − | − | + | − | − | − | − | − | − | − |
| | 1.56 | − | − | + | + | + | + | + | + | + | + | + |
| | 0.78 | − | − | + | + | + | + | + | + | + | + | + |
| | 0.39 | − | − | + | + | + | + | + | + | + | + | + |
| | 0.20 | − | − | + | + | + | + | + | + | + | + | + |
| | 0 | − | − | + | + | + | + | + | + | + | + | |

TABLE 34

Bacterial strain used: MRSA-2
Inoculum size: $10^6$ cells/ml
(Unit: μg/ml)

| | | Zinc chloride | | | | | | | | | | |
|---|---|---|---|---|---|---|---|---|---|---|---|---|
| | | 800 | 400 | 200 | 100 | 50 | 25 | 12.5 | 6.25 | 3.13 | 1.56 | 0 |
| Hinoki-tiol | 200 | − | − | − | − | − | − | − | − | − | − | − |
| | 100 | − | − | − | − | − | − | − | − | − | − | − |
| | 50 | − | − | − | − | − | − | − | − | − | − | + |
| | 25 | − | − | − | − | − | − | − | + | + | + | + |
| | 12.5 | − | − | − | − | − | − | − | − | − | − | − |
| | 6.25 | − | − | − | − | − | − | − | − | − | − | − |
| | 3.13 | − | − | − | − | − | − | − | − | − | − | − |
| | 1.56 | − | − | + | + | + | + | + | + | + | + | + |
| | 0.78 | − | − | + | + | + | + | + | + | + | + | + |
| | 0.39 | − | − | + | + | + | + | + | + | + | + | + |
| | 0.20 | − | − | + | + | + | + | + | + | + | + | + |
| | 0 | − | − | + | + | + | + | + | + | + | + | |

TABLE 35

Bacterial strain used: MRSA-3
Inoculum size: $10^6$ cells/ml
(Unit: μg/ml)

| | | Zinc oxide | | | | | | | | | | |
|---|---|---|---|---|---|---|---|---|---|---|---|---|
| | | 800 | 400 | 200 | 100 | 50 | 25 | 12.5 | 6.25 | 3.13 | 1.56 | 0 |
| Hinoki-tiol | 200 | − | − | − | − | − | − | − | − | − | − | − |
| | 100 | − | − | − | − | − | − | − | − | − | − | − |
| | 50 | − | − | − | − | − | − | − | − | − | − | + |
| | 25 | − | − | − | − | − | − | − | − | + | + | + |
| | 12.5 | − | − | − | − | − | − | − | − | − | − | − |
| | 6.25 | − | − | − | − | − | − | − | − | − | − | − |
| | 3.13 | − | − | − | − | − | − | − | − | − | − | − |
| | 1.56 | − | − | − | + | + | + | + | + | + | + | + |
| | 0.78 | − | − | − | + | + | + | + | + | + | + | + |
| | 0.39 | − | − | − | + | + | + | + | + | + | + | + |
| | 0.20 | − | − | − | + | + | + | + | + | + | + | + |
| | 0 | − | − | − | + | + | + | + | + | + | + | |

TABLE 36

Bacterial strain used: MRSA-1
Inoculum size: $10^6$ cells/ml
(Unit: μg/ml)

| | | Zinc sulfate heptahydrate | | | | | | | | | | |
|---|---|---|---|---|---|---|---|---|---|---|---|---|
| | | 1600 | 800 | 400 | 200 | 100 | 50 | 25 | 12.5 | 6.25 | 3.13 | 0 |
| Hinoki-tiol | 200 | − | − | − | − | − | − | − | − | − | − | − |
| | 100 | − | − | − | − | − | − | − | − | − | − | − |
| | 50 | − | − | − | − | − | − | − | − | − | + | + |
| | 25 | − | − | − | − | − | − | + | + | + | + | + |
| | 12.5 | − | − | − | − | − | − | − | − | − | − | − |
| | 6.25 | − | − | − | − | − | − | − | − | − | − | − |
| | 3.13 | − | − | − | + | − | − | − | − | − | − | − |
| | 1.56 | − | − | + | + | + | + | + | + | + | + | + |
| | 0.78 | − | − | + | + | + | + | + | + | + | + | + |
| | 0.39 | − | − | + | + | + | + | + | + | + | + | + |
| | 0.20 | − | − | + | + | + | + | + | + | + | + | + |
| | 0 | − | − | + | + | + | + | + | + | + | + | |

TABLE 37

Bacterial strain used: MRSA-2
Inoculum size: $10^6$ cells/ml
(Unit: μg/ml)

| | | Zinc sulfate heptahydrate | | | | | | | | | | |
|---|---|---|---|---|---|---|---|---|---|---|---|---|
| | | 1600 | 800 | 400 | 200 | 100 | 50 | 25 | 12.5 | 6.25 | 3.13 | 0 |
| Hinoki- | 200 | − | − | − | − | − | − | − | − | − | − | − |
| tiol | 100 | − | − | − | − | − | − | − | − | − | − | − |
| | 50 | − | − | − | − | − | − | − | − | − | + | + |
| | 25 | − | − | − | − | − | − | − | + | + | + | + |
| | 12.5 | − | − | − | − | − | − | − | − | − | − | − |
| | 6.25 | − | − | − | − | − | − | − | − | − | − | − |
| | 3.13 | − | − | − | − | − | − | − | − | − | − | − |
| | 1.56 | − | − | + | + | + | + | + | + | + | + | + |
| | 0.78 | − | − | + | + | + | + | + | + | + | + | + |
| | 0.39 | − | − | + | + | + | + | + | + | + | + | + |
| | 0.20 | − | − | + | + | + | + | + | + | + | + | + |
| | 0 | − | − | + | + | + | + | + | + | + | + | |

TABLE 38

Bacterial strain used: MRSE-1
Inoculum size: $10^6$ cells/ml
(Unit: μg/ml)

| | | Zinc sulfate heptahydrate | | | | | | | | | | |
|---|---|---|---|---|---|---|---|---|---|---|---|---|
| | | 1600 | 800 | 400 | 200 | 100 | 50 | 25 | 12.5 | 6.25 | 3.13 | 0 |
| Hinoki- | 200 | − | − | − | − | − | − | − | − | − | − | − |
| tiol | 100 | − | − | − | − | − | − | − | − | − | − | − |
| | 50 | − | − | − | − | − | − | − | − | − | − | − |
| | 25 | − | − | − | − | − | − | − | − | − | + | + |
| | 12.5 | − | − | − | − | − | − | − | − | − | − | − |
| | 6.25 | − | − | − | − | − | − | − | − | − | − | − |
| | 3.13 | − | − | − | − | − | − | − | − | − | − | − |
| | 1.56 | − | − | − | − | − | − | − | − | − | − | − |
| | 0.78 | − | − | − | − | + | + | + | + | + | + | + |
| | 0.39 | − | − | − | + | + | + | + | + | + | + | + |
| | 0.20 | − | − | − | + | + | + | + | + | + | + | + |
| | 0 | − | − | − | + | + | + | + | + | + | + | |

We claim:

1. An antibacterial composition comprising an effective amount of a combination of (a) at least one zinc compound selected from the group consisting of zinc oxide, zinc myristate, zinc chloride, zinc sulfate, a zinc-nicotinamide complex, a zinc-bishistidine complex, zinc nitrate, zinc salicylate, zinc lactate and zinc phosphate, and (b) at least one compound selected from the group consisting of hinokitiol and salts thereof, wherein, based on the total amount of said at least one zinc compound and said at least one compound selected from the group consisting of hinokitiol and salts thereof, said at least one zinc compound is present in an amount of about 50 to 99.9% by weight and said at least one compound selected from the group consisting of hinokitiol and salts thereof is present in an amount of about 50 to 0.1% by weight.

2. The antibacterial composition as claimed in claim 1, wherein said hinokitiol salt is least one salt selected from the group consisting of a sodium salt, a potassium salt, a magnesium salt, a copper salt, a zinc salt, a diethanolamine salt, a 2-amino-2-ethyl-1,3-propanediol salt, a triethanolamine salt, a morpholine salt, a piperazine salt, a piperidine salt, an ammonium salt, an arginine salt, a lysine salt and a histidine salt.

3. The antibacterial composition as claimed in claim 2, wherein said at least one zinc compound is zinc oxide, and wherein, based on the total amount of said zinc oxide and said at least one compound selected from the group consisting of hinokitiol and salts thereof, said zinc oxide is present in an amount of about 50 to 99.9 by weight and said at least one compound selected from the group consisting of hinokitiol and salts thereof is present in an amount of about 50 to 0.1 by weight.

4. A cosmetic having anti-bacterial/antifungal activity comprising an effective amount of a combination of (a) at least one zinc compound selected from the group consisting of zinc oxide, zinc myristate, zinc chloride, zinc sulfate, a zinc-nicotinamide complex, a zinc-bishistidine complex, zinc nitrate, zinc salicylate, zinc lactate and zinc phosphate, and (b) at least one compound selected from the group consisting of hinokitiol and salts thereof, wherein, based on the total amount of said at least one zinc compound and said at least one compound selected from the group consisting of hinokitiol and salts thereof, said at least one zinc compound is present in an amount of about 50 to 99.9% by weight and said at least one compound selected from the group consisting of hinokitiol and salts thereof is present in an amount of about 50 to 0.1% by weight.

5. The cosmetic as claimed in claim 4, wherein said hinokitiol salt is at least one salt selected from the group consisting of a sodium salt, a potassium salt, a magnesium salt, a copper salt, a zinc salt, a diethanolamine salt, a 2-amino-2-ethyl-1,3-propanediol salt, a triethanolamine salt, a morpholine salt, a piperazine salt, a piperidine salt, an ammonium salt, an arginine salt, a lysine salt and a histidine salt.

6. The cosmetic as claimed in claim 5, wherein said at least one zinc compound is zinc oxide and wherein, based on the total amount of said zinc oxide and said at least one compound selected from the group consisting of hinokitiol and salts thereof, said zinc oxide is present in an amount of about 50 to 99.9% by weight and said at least one compound selected from the group consisting of hinokitiol and salts thereof is present in an amount of about 50 to 0.1% by weight.

7. A method of controlling bacteria which comprises the step of using an effective amount of a combination of (a) at least one zinc compound selected from the group consisting of zinc oxide, zinc myristate, zinc chloride, zinc sulfate, a zinc-nicotinamide complex, a zinc-bishistidine complex, zinc nitrate, zinc salicylate, zinc lactate and zinc phosphate and (b) at least one compound selected from the group consisting of hinokitiol and salts thereof, wherein, based on the total amount of said at least one zinc compound and said at least one compound selected from the group consisting of hinokitiol and salts thereof, said at least one zinc compound is used in an amount of about 50 to 99.9% by weight and said at least one compound selected from the group consisting of hinokitiol and salts thereof is used in an amount of about 50 to 0.1% by weight.

8. The method as claimed in claim 7, wherein said hinokitiol salt is at least one salt selected from the group consisting of a sodium salt, a potassium salt, a magnesium salt, a copper salt, a zinc salt, a diethanolamine salt, a 2-amino-2-ethyl-1,3-propanediol salt, a triethanolamine salt, a morpholine salt, a piperazine salt, a piperidine salt, an ammonium salt, an arginine salt, a lysine salt and a histidine salt.

9. The method as claimed in claim 8, wherein said at least one zinc compound is zinc oxide and wherein, based on the total amount of said zinc oxide and said at least one compound selected from the group consisting of hinokitiol and salts thereof, said zinc oxide is used in an amount of about 50 to 99.9% by weight and said at least one compound selected from the group consisting of hinokitiol and salts thereof is used in an amount of about 50 to 0.1% by weight.

10. The method as claimed in claim 8, wherein said bacteria are resistant to one or more antibiotics.

11. The method as claimed in claim 9, wherein said bacteria are resistant to one or more antibiotics.

12. The method as claimed in claim 10, wherein said bacteria, which are resistant to one or more antibiotics, are methicillin-resistant *Staphylococcus aureus* or methicillin-resistant *Staphylococcus epidermidis*.

13. The method as claimed in claim 11, wherein said bacteria, which are resistant to one or more antibiotics, are methicillin-resistant *Staphylococcus aureus* or methicillin-resistant *Staphylococcus epidermidis*.

14. A method for treating an infectious disease caused by bacteria in a patient comprising administering to said patient an effective amount of a combination of (a) at least one zinc compound selected from the group consisting of zinc oxide, zinc myristate, zinc chloride, zinc sulfate, a zinc-nicotinamide complex, a zinc-bishistidine complex, zinc nitrate, zinc salicylate, zinc lactate and zinc phosphate and (b) at least one compound selected from the group consisting of hinokitiol and salts thereof, and wherein, based on the total amount of said at least one zinc compound and said at least one compound selected from the group consisting of hinokitiol and salts thereof, said at least one zinc compound is administered in an amount of about 50 to 99.9% by weight and said at least one compound selected from the group consisting of hinokitiol and salts thereof is administered in an amount of about 50 to 0.1% by weight.

15. The method as claimed in claim 14, wherein said hinokitiol salt is at least one salt selected from the group consisting of a sodium salt, a potassium salt, a magnesium salt, a copper salt, a zinc salt, a diethanolamine salt, a 2-amino-2-ethyl-1,3-propanediol salt, a triethanolamine salt, a morpholine salt, a piperazine salt, a piperidine salt, an ammonium salt, an arginine salt, a lysine salt and a histidine salt.

16. The method as claimed in claim 15, wherein said at least one zinc compound is zinc oxide, and wherein, based on the total amount of said zinc oxide and said at least one compound selected from the group consisting of hinokitiol and salts thereof, said zinc oxide is administered in an amount of about 50 to 99.9% by weight and said at least one compound selected from the group consisting of hinokitiol and salts thereof is administered in an amount of about 50 to 0.1% by weight.

17. A method for preserving a cosmetic comprising the step of adding to a cosmetic an effective amount of a combination of (a) at least one zinc compound selected from the group consisting of zinc oxide, zinc myristate, zinc chloride, zinc sulfate, a zinc-nicotinamide complex, a zinc-bishistidine complex, zinc nitrate, zinc salicylate, zinc lactate and zinc phosphate and (b) at least one compound selected from the group consisting of hinokitiol and salts thereof, wherein, based on the total amount of said at least one zinc compound and said at least one compound selected from the group consisting of hinokitiol and salts thereof, said at least one zinc compound is used in an amount of about 50 to 99.9% by weight and said at least one compound selected from the group consisting of hinokitiol and salts thereof is added in an amount of about 50 to 0.1% by weight.

18. The method as claimed in claim 17, wherein said hinokitiol salt is at least one salt selected from the group consisting of a sodium salt, a potassium salt, a magnesium salt, a copper salt, a zinc salt, a diethanolamine salt, a 2-amino-2-ethyl-1,3-propanediol salt, a triethanolamine salt, a morpholine salt, a piperazine salt, a piperidine salt, an ammonium salt, an arginine salt, a lysine salt and a histidine salt.

19. The method as claimed in claim 18, wherein said at least one zinc compound is zinc oxide, and wherein, based on the total amount of said zinc oxide and said at least one compound selected from the group consisting of hinokitiol and salts thereof, said zinc oxide is used in an amount of about 50 to 99.9 by weight and said at least one compound selected from the group consisting of hinokitiol and salts thereof is added in an amount of about 50 to 0.1% by weight.

20. The cosmetic as claimed in claim 4 having antibacterial activity.

* * * * *

UNITED STATES PATENT AND TRADEMARK OFFICE
CERTIFICATE OF CORRECTION

PATENT NO. : 5,696,169
DATED : December 9, 1997
INVENTOR(S) : Yoshiro Otsu, Yaeno Arima and Yoriko Nakai It is certified that error appears in the above-identified patent and that said Letters Patent is hereby corrected as shown below:

On the title page:

Item [30], insert --March 13, 1992 [JP] Japan.... 55074
August 11, 1992 [JP] Japan...213841--.

Column 35, lines 33 to 42, in the table "Result of MIC" replace each occurance of "<100" with -->100--.

Signed and Sealed this

Twenty-sixth Day of January, 1999

Attest:

Attesting Officer

*Acting Commissioner of Patents and Trademarks*